US011202997B2

(12) United States Patent
Flood

(10) Patent No.: US 11,202,997 B2
(45) Date of Patent: Dec. 21, 2021

(54) DILUTION DEVICE FOR DISPENSING FLUID

(71) Applicant: Sonny's HFI Holdings, LLC, Wilmington, DE (US)

(72) Inventor: Bryan Flood, Minneapolis, MN (US)

(73) Assignee: Sonny's HFI Holdings, LLC, Wilmington, DE (US)

( * ) Notice: Subject to any disclaimer, the term of this patent is extended or adjusted under 35 U.S.C. 154(b) by 174 days.

(21) Appl. No.: 16/039,982

(22) Filed: Jul. 19, 2018

(65) Prior Publication Data

US 2019/0022607 A1 Jan. 24, 2019

Related U.S. Application Data

(60) Provisional application No. 62/534,830, filed on Jul. 20, 2017.

(51) Int. Cl.
*B01F 5/06* (2006.01)
*B01F 5/04* (2006.01)
(Continued)

(52) U.S. Cl.
CPC ............ *B01F 5/0604* (2013.01); *B01F 5/043* (2013.01); *B01F 5/0415* (2013.01);
(Continued)

(58) Field of Classification Search
CPC ............ B01F 15/00935; B01F 15/0261; B01F 2003/0896; B01F 5/0415; B01F 5/043; B01F 5/0604
See application file for complete search history.

(56) References Cited

U.S. PATENT DOCUMENTS 2,021,079 A * 11/1935 Mittendorf ............ F25B 41/067 138/42
2,118,290 A * 5/1938 Black .................. G05D 16/103 138/42

(Continued)

FOREIGN PATENT DOCUMENTS

EP 0076451 A1 4/1983

OTHER PUBLICATIONS

International Search Report and Written Opinion dated Oct. 12, 2018 in connection with International Patent Application No. PCT/US2018/042879, 16 pages.

(Continued)

*Primary Examiner* — Tony G Soohoo
(74) *Attorney, Agent, or Firm* — Dorsey & Whitney LLP

(57) ABSTRACT

A dilution device may include a first component and a second component. The first component may define a groove including an inlet portion and an outlet portion. The second component may define an inlet in fluid communication with the inlet portion of the first component and an outlet in fluid communication with the outlet portion of the first component. Relative rotation between the first component and the second component may cause relative movement between the outlet and the outlet portion that changes the effective length of the groove fluidly coupling the inlet and the outlet of the second component. The cross-sectional area of the groove may vary along a length of the groove to provide different flow characteristics depending on the effective length of the groove.

10 Claims, 19 Drawing Sheets

(51) Int. Cl.
*B01F 15/02* (2006.01)
*B01F 3/08* (2006.01)

(52) U.S. Cl.
CPC ........ *B01F 5/0644* (2013.01); *B01F 15/0261* (2013.01); *B01F 15/0284* (2013.01); *B01F 2003/0896* (2013.01); *B01F 2215/0431* (2013.01)

(56) References Cited

U.S. PATENT DOCUMENTS 2,118,295 A * 5/1938 Crawford ............. G05D 16/103 138/42
2,236,084 A * 3/1941 Brown ................ F16L 55/0338 138/43
2,506,179 A * 5/1950 Taplin ................... G05B 11/011 138/43
2,833,311 A * 5/1958 Baldelli .................... F16K 1/04 138/43
2,850,038 A * 9/1958 Shabaker ............. G05D 7/0113 137/505.13
3,190,618 A * 6/1965 Katzen .................. B01F 5/0659 366/337
3,323,550 A * 6/1967 Lee, II ...................... F15C 1/16 138/39
3,375,855 A * 4/1968 Deeks ................... F22B 37/545 138/42
3,386,458 A * 6/1968 Wasserman ............... B01F 3/02 137/114
3,532,126 A * 10/1970 Boothe ..................... F15C 1/02 138/43
3,532,127 A * 10/1970 Bottone, Jr. ...... A61M 5/16877 138/43
3,608,571 A * 9/1971 Wilcox ..................... F15C 1/16 137/809
3,744,762 A * 7/1973 Schlicht ................ B01F 5/0663 366/338
3,806,097 A * 4/1974 Devellian ............ B01F 5/0647 366/339
3,998,427 A * 12/1976 Bentley ................ A01G 25/023 251/208
4,226,368 A * 10/1980 Hunter ................. A01G 25/023 239/542
4,267,045 A * 5/1981 Hoof ...................... B01D 25/26 137/625.37
4,514,095 A * 4/1985 Ehrfeld ............. F16L 55/02718 138/42
4,738,665 A * 4/1988 Shepard ............ A61M 5/16881 137/1
4,917,687 A * 4/1990 O'Boyle ........... A61M 5/16881 138/43
5,005,604 A 4/1991 Aslanian
5,036,880 A * 8/1991 Safford ............... F04B 39/1053 137/516.21
5,287,891 A * 2/1994 Bourlon ................ F16L 55/027 138/40
5,887,977 A * 3/1999 Morikawa ............. B01F 5/0604 138/42
6,095,196 A * 8/2000 McCarty ................... F15D 1/02 137/625.3
6,238,081 B1 * 5/2001 Sand .................... A01G 25/023 138/43
6,244,297 B1 * 6/2001 Baumann ................ F16K 47/08 137/625.3
6,499,872 B2 * 12/2002 Sand .................... A01G 25/023 366/160.1
7,520,661 B1 * 4/2009 Lawson ................ B01F 5/0604 138/42
7,789,108 B1 * 9/2010 Lawson .............. B01F 13/0059 138/42
7,909,502 B2 * 3/2011 Ehrfeld ................. B01F 5/0604 366/340
8,439,282 B2 * 5/2013 Allen ................... A01G 25/023 239/570
9,258,949 B2 * 2/2016 Nourian ............... A01G 25/023
9,561,481 B2 * 2/2017 Schlueter ................ B01F 5/043
9,943,815 B2 * 4/2018 Matsumoto .............. A01K 7/00
10,589,236 B2 * 3/2020 Mochizuki .......... B01F 7/00458
2001/0015231 A1 * 8/2001 Sand ..................... B01F 5/0415 138/42
2003/0039169 A1 * 2/2003 Ehrfeld ................. B01F 5/0604 366/336
2004/0182436 A1 * 9/2004 Graham ............... G05D 7/0186 137/119.1
2005/0104024 A1 * 5/2005 Oliver ..................... F16K 3/085 251/206
2013/0128688 A1 * 5/2013 Doolin .................. B01F 5/0613 366/163.2
2015/0137017 A1 5/2015 Ambrosina et al.
2019/0022607 A1 * 1/2019 Flood .................... B01F 5/0415

OTHER PUBLICATIONS

Examination Report dated Nov. 16, 2020 in connection with European patent application No. 18750054.1, 7 pages.
Examination Report dated Apr. 13, 2021 in connection with European patent application No. 18750054.1, 10 pages.
Examination Report dated Oct. 4, 2021 in connection with European patent application No. 18750054.1, 7 pages.

* cited by examiner

DILUTION DEVICE FOR DISPENSING FLUID

TECHNICAL FIELD

The present disclosure relates to fluid metering, such as fluid metering at low dilution ratios and draw rates. More particularly, the present disclosure relates to a dilution device for dispensing fluid, such as a chemical for use in the car wash industry.

BACKGROUND

Chemicals and especially chemicals used in the car wash industry have become increasingly concentrated in order to reduce material handling concerns and shipping costs of those chemicals. Most concentrated chemicals are diluted with water prior to or during application. For more concentrated chemicals, the dilution ratios have increased (i.e., less chemical, more water).

Traditionally chemicals have been metered by use of a pump or a small hole that restricts the flow of chemical. Typically, the diameter of the hole is changed to provide a desired flow of chemical. Alternatively, the length (depth) of the hole has been changed to create more drag on a fluid flowing through the hole, thereby restricting the flow of chemical through the hole (this is commonly referred to as a capillary or metering tube). Metering tubes typically use a larger diameter hole and can be less susceptible to clogging from small particulate as it merely passes through the larger diameter hole, but metering tubes are often very long and difficult to use as they must be cut to length.

As dilution ratios increase based on the use of more concentrated chemicals, it becomes increasingly difficult to provide accurate and consistent flow of chemical to a dilution device. For example, many dilution devices are unable to achieve sufficiently low draw rates to provide a desired mixture of chemical and water, and thus the mixture includes extraneous chemical. The more concentrated chemicals are expensive, and thus it is desirable to use as little chemical as possible. To wash a car, typically 30 to 60 milliliters (ml) of standard concentrate chemical and 0.5 to 2.5 gallons of water are used in a single 30-second application, whereas only 3 to 10 ml of more concentrated chemical may be used in a similar time. The use rate recommendations by the chemical manufacturers are trending lower, but the technology for metering the chemical has not been able to keep up with the ability to further concentrate the chemical.

Traditional dilution devices lack sufficient accuracy for metering the more concentrated chemicals. Many devices include incremental adjustments for dilution ratio. However, as the recommended use rates of chemical are lowered, the adjustment increments are more inaccurate on a percentage basis. For example, for a dilution device that is adjustable in 6 ml increments, this adjustment increment (6 ml) is 20% of a 30 ml chemical draw, but it is 100% of a 6 ml chemical draw. The inability to accurately adjust for a proper amount of chemical results in chemical waste.

Additionally, as the dilution ratios increase, it is more difficult to fully and evenly mix chemical with water. In other words, it is harder to completely and evenly mix 3 ml of chemical with one gallon of water than it is to mix 30 ml of chemical with one gallon of water. Thus, the variation in dilution ratio throughout the diluted mixture increases as the dilution ratios increase. These variations in dilution ratio create pockets of rich and lean chemical dilutions that are wasteful because the metering device has to be set at a lower dilution ratio (more chemical, less water) that ensures the areas in the mixture with the lowest chemical content are sufficient to clean the car.

Moreover, to decrease the chemical draws, dilution devices typically use smaller and smaller passageways and orifices to meter the chemical. Particulate in the chemical is more likely to clog these passageways and orifices in the dilution device, causing operational concerns as a clogged dilution device does not produce the correct concentration of chemical. Dilution devices for low flows typically use a small size metering diameter in the 0.005 inch range, which is easily clogged by very fine particulate.

Related devices may be described in U.S. Pat. Nos. 3,532,126, 3,532,127, 4,917,687, 6,238,081, and 9,258,949.

SUMMARY

In some embodiments, a dilution device is provided. The dilution device may include a metering component defining a metering groove with flow characteristics that vary along a length of the groove. For example, the depth and/or the width of the groove may vary along the length of the groove to provide different flow characteristics along the length of the groove. Additionally or alternatively, the metering groove may change directions along its length to provide different flow characteristics along the length of the groove. The dilution device may include another component defining an inlet and an outlet, and the groove may at least partially define a flow path between the inlet and the outlet. The outlet may be alignable with different portions of the groove to change the effective length of the groove that fluidly couples the inlet and the outlet.

In some examples, a dilution device according to embodiments of the present disclosure may include a first component defining a groove including an inlet portion and an outlet portion, and a second component defining an inlet in fluid communication with the inlet portion of the first component and an outlet in fluid communication with the outlet portion of the first component. Relative rotation between the first component and the second component may cause relative movement between the outlet and the outlet portion that changes the effective length of the groove fluidly coupling the inlet and the outlet of the second component. The cross-sectional area of the groove may vary along a length of the groove to provide different flow restriction depending on the effective length of the groove.

In some examples, the depth and the width of the groove may vary along the length of the groove. In some embodiments, the groove can travel along a tortuous path with multiple direction changes. In some examples, the first component comprises a metering disc. In some embodiments, the relative rotation between the first component and the second component is automatically controlled without user intervention. In some examples, the second component comprises a first housing coupled with a second housing, the first housing defining an aperture and the second housing defining the inlet and the outlet.

In some embodiments, a dilution device also includes an adjustment feature configured to cause the relative rotation between the first component and the second component responsive to user manipulation. In some examples, the adjustment feature comprises a slot. In some examples, the dilution device also includes a biasing element configured to bias the first component against an internal surface of the second component. In some embodiments, the biasing element comprises a wave spring. In some examples, the outlet portion comprises a plurality of outlet portion segments radially distributed around a surface of the first component. In some embodiments, the plurality of outlet portion segments are evenly spaced with respect to each other.

According to some embodiments of the present disclosure, a dilution system may include a dilution device defining a flow channel in fluid communication with a concentrated chemical, and an eductor in fluid communication with the flow channel and a motive fluid. The motive fluid may flow through the eductor and create a suction force that draws the concentrated chemical into the flow path of the motive fluid to mix the concentrated chemical with the motive fluid.

In some examples, the dilution system further comprises at least two sealing elements that create a fluid-tight interface between the dilution device and the eductor. In some embodiments, the dilution system also includes a control system configured to adjust the amount of concentrated chemical drawn into the flow path of the motive fluid without user intervention. In some examples, the dilution device can be rotatable with respect to the eductor. In some embodiments, the flow channel can be configured to adjust a flow rate of the concentrated chemical through the dilution device upon rotation thereof.

According to some embodiments of the present disclosure, a method of diluting a chemical concentrate with a fluid may involve biasing a metering disc into engagement with an eductor body to form a flow channel between the metering disc and the eductor body. The method may also involve sealing the flow channel by deforming one of the metering disc or the eductor body with ridges on the other of the metering disc or the eductor that extend along edges of the flow channel. The method may further involve rotating the metering disc relative to an eductor body to change an effective length of a metering groove fluidly coupling a concentrated chemical and a motive fluid to vary dilution of the concentrated chemical. In some examples, rotating the metering disc relative to the eductor body comprises autonomously rotating the metering disc based one or more monitored conditions

DETAILED DESCRIPTION

Figure 1:
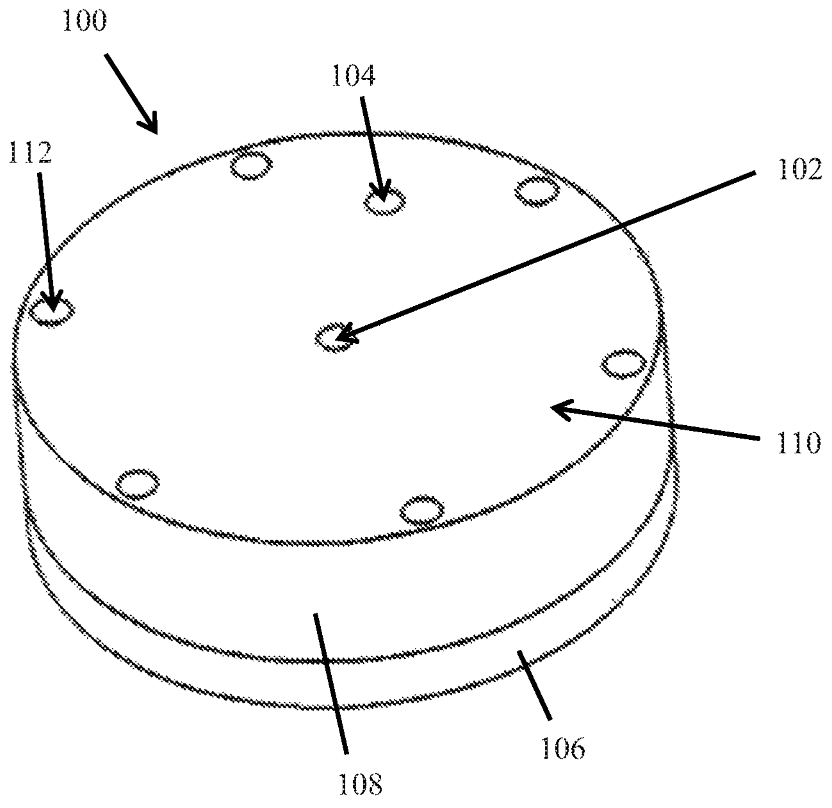
FIG. 1 is a schematic illustration of a dilution device, according to certain implementations.

Described herein is a device that meters a concentrated substance such as one or more chemicals, gases, soaps, detergents, rinsing agents, foaming agents, and/or liquid waxes. For convenience without an intent to limit, the concentrated substance will be referred to herein as a chemical. The device may use a combination of length and cross-sectional area variations of a flow channel to meter the flow of chemical to a chemical mixing device, such as a Venturi. By combining the effect of cross-sectional area and length variations of a flow channel, the device may be compact and may include a flow channel with relatively short effective lengths and a relatively larger cross-sectional area that more easily passes particulate.

The length of the flow channel can be shortened or elongated by relative movement between two or more components of the device. The chemical flow rate initially may change quickly as a flow channel increases in length, and after the initial change the flow rate of chemical may change less quickly as the length of the flow channel increases further. In certain implementations, the device includes a metering component (such as a disc, sleeve, slide, or other component) that is incrementally adjustable to provide incremental adjustment of the effective length of the flow channel. In certain implementations, the device includes a metering component that is continuously adjustable to provide continuous adjustment of the effective length of the flow channel. The metering component may include a flow channel with a cross-sectional area that varies along the length of the flow channel to provide additional adjustment of the chemical flow rate. Thus, relative rotation between two components of the device can vary at least two parameters of the flow channel: its effective length and its effective cross-sectional area. The cross-sectional shape of the flow channel may be circular or non-circular. Different metering components with different configurations may be used to provide different flow rates and metering ranges. The metering component may be formed from various types of materials, such as stainless steel, hastelloy-C, or other chemical compatible materials.

The device may be configured to seal the flow channel to an adjacent surface so that chemical does not leak out of the flow channel. For example, the device may include flat, relatively-hard surfaces that collectively define a flow channel therebetween. As another example, the device may include a harder surface and a softer surface that is deformable by the harder surface. Small ridges may be formed in the harder surface, and the small ridges may engage the softer surface along opposing edges of a metering groove to deform the softer surface and form a seal between the harder surface and the softer surface. The small ridges may deform the softer surface by high contact pressure and may at least partially create the groove. The harder surface and/or the softer surface may be injection molded out of inexpensive and highly chemical compatible plastics, such as high-density polyethylene (HDPE). In certain implementations, the softer surface may be formed from an elastomer.

An eductor may be attached to the device, allowing concentrated chemicals, gases, or other materials to be mixed with a motive fluid such as water. Accurately-diluted fluid mixtures may be emitted through the eductor outlet. By creating a fluid-tight seal between the device and the eductor, the combined device and eductor may be more resistant to leaks than pre-existing apparatus. Features from any of the disclosed embodiments may be used in combination with one another, without limitation. In addition, other features and advantages of the present disclosure will become apparent to those of ordinary skill in the art through consideration of the following detailed description and the accompanying drawings.

FIG. 1 is a schematic illustration of a dilution device 100 for dispensing fluid, such as a metering device for dispensing car wash solution. The dilution device 100 includes an inlet 102 and an outlet 104. The inlet 102 may be in fluid communication with a chemical, which may be stored in a chemical container at atmospheric pressure. The outlet 104 may be in fluid communication with the inlet 102 via a flow channel, which is described in more detail below. The outlet 104 also may be in fluid communication with a chemical mixing device, such as an eductor. For example, the outlet 104 may be fluidly coupled with a chemical inlet of an eductor. In certain implementations, the chemical inlet of the eductor typically draws 25 to 28 inches of mercury (inHg) of vacuum with an inlet water pressure of 200 pound force per square inch (psi). The difference between the vacuum in the eductor and the atmospheric pressure at the inlet 102 creates a pressure differential that draws chemical thru the dilution device 100.

As illustrated in FIG. 1, the dilution device 100 may include a first housing component 106 and a second housing component 108. The first housing component 106 may function as a cover for the second housing component 108. In certain implementations, the first housing component 106 may be formed as a plate. The inlet 102 and the outlet 104 may be formed as thru-holes that extend through the second housing component 108. As shown in FIG. 1, the inlet 102 and the outlet 104 may open through an exterior surface 110, such as a bottom surface, of the second housing component 108. The outer surface 110 may be planar (i.e., flat), and may be formed of machined polyethylene. The inlet 102 may be located at a center of the outer surface 110 of the second housing component 108, and the outlet 104 may be located radially outward from the inlet 102. The first housing component 106 and the second housing component 108 may be coupled together with one or more fasteners, such as screws. The one or more fasteners may be received in one or more holes 112 arranged around a peripheral portion of the first and second housing components 106, 108 radially outward of the inlet 102 and the outlet 104.

Figure 2:
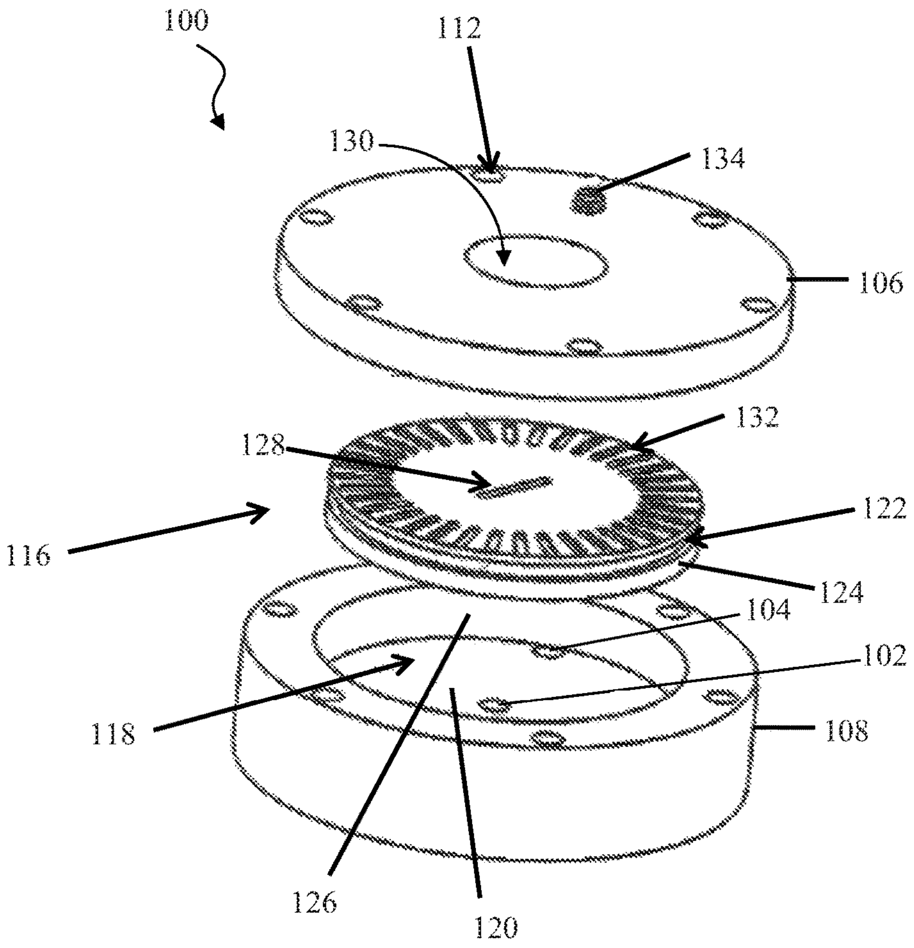
FIG. 2 is a schematic illustration of an exploded view of the dilution device of FIG. 1, according to certain implementations.

FIG. 2 is a schematic illustration of an exploded view of the dilution device 100. As illustrated in FIG. 2, the dilution device 100 includes a metering component, such as metering disc 116. The metering disc 116 may be received in a cavity 118 formed at least partially in the second housing component 108. The inlet 102 and the outlet 104 may open through an interior surface 120 of the second housing component 108 into the cavity 118. The interior surface 120 may be planar (i.e., flat). The metering disc 116 may sealingly engage the second housing component 108 to maintain fluid flow between the inlet 102 and the outlet 104 with little to no leaking. For example, a sealing element may be retained in a groove 122 formed in a circumferential surface 124 of the metering disc 116, and the sealing element may engage a corresponding circumferential surface 126 of the second housing component 108 to form a fluid-tight seal between the metering disc 116 and the second housing component 108. The circumferential surface 126 may extend orthogonally to the interior surface 120. The interior surface 120 may form a fluid-tight seal with a corresponding surface of the metering disc 116, as described in more detail below.

The metering disc 116 may be rotatable relative to the first housing component 106, the second housing component 108, or both. As illustrated in FIG. 2, the metering disc 116 may include a user engagement feature 128 to facilitate rotating the metering disc 116 relative to the second housing component 108. The user engagement feature 128, such as the illustrated adjustment slot, may be accessible through an aperture 130 formed through the first housing component 106. The metering disc 116 may provide continuous or discrete adjustment relative to the second housing component 108. In certain implementations, the metering disc 116 may include an increment feature 132, such as a series of detent grooves, that work in conjunction with a corresponding increment feature 134, such as a detent ball, of the first housing component 106 to provide consistent and reliable angularly increments, such as 10 degree increments, of the metering disc 116 relative to the second housing component 108. The increment features 132, 134 may be omitted for implementations where the adjustment is analog and not discrete.

Figure 3A:
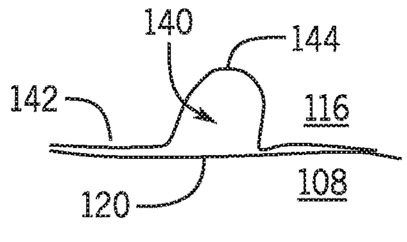
FIGS. 3A and 3B are schematic illustrations of a cross-sectional view of a flow channel of the dilution device of FIG. 1, according to certain implementations.
Figure 3B:
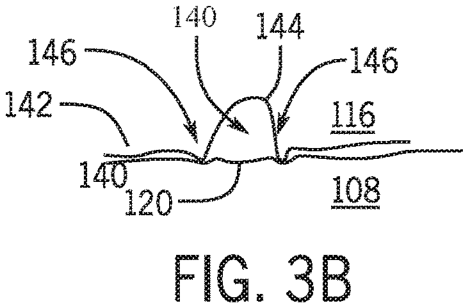

FIGS. 3A and 3B are schematic illustrations of a cross-sectional view of a flow channel 140 of the dilution device 100. The flow channel 140 may fluidly couple the inlet 102 and the outlet 104. The flow channel 140 may be formed between confronting surfaces of the metering disc 116 and the second housing component 108. For example, the flow channel 140 may be formed collectively by the interior surface 120 of the second housing component 108 and a corresponding surface 142 of the metering disc 116. In certain implementations, the metering disc 116 may define a groove 144 that determines a flow path for chemical to flow between the inlet 102 and the outlet 104. To maintain chemical in the flow channel 140, the corresponding surfaces 120, 142 of the second housing component 108 and the metering disc 116, respectively, may form a fluid-tight seal along the edges of the groove 144. For example, the surfaces 120, 142 may be formed as flat surfaces with tight tolerances to form a fluid-tight interface between the surfaces 120, 142. For example, the surface 120, the surface 142, or both may be flat within 0.0002 of an inch, resulting in a typical leak rate of less than 1 ml of water per minute. Less flatness typically results in more leakage internal to the disc 116, and thus less capability to meter chemical to sufficiently low values for ultra-concentrated chemical. Additionally or alternatively, a seal feature may be formed along the edges of the groove 144. For example, as illustrated in FIG. 3B, a ridge 146 may extend along each edge of the groove 144. The ridges 146 may protrude from the surface 142 of the metering disc 116 and may sealingly engage the interior surface 120 of the second housing component 108 to substantially prevent chemical from escaping the flow channel 140. The surfaces 120, 142 may be formed from materials that facilitate a fluid-tight interface therebetween. For example, in certain implementations, the surface 142 of the metering disc 116 is formed of metal, such as stainless steel, and the interior surface 120 of the second housing component 108 is formed of polyethylene to promote sealing between the surfaces 120, 142. The groove 144 may be formed in the surface 142 in various manners, such as end milling.

Figure 4:
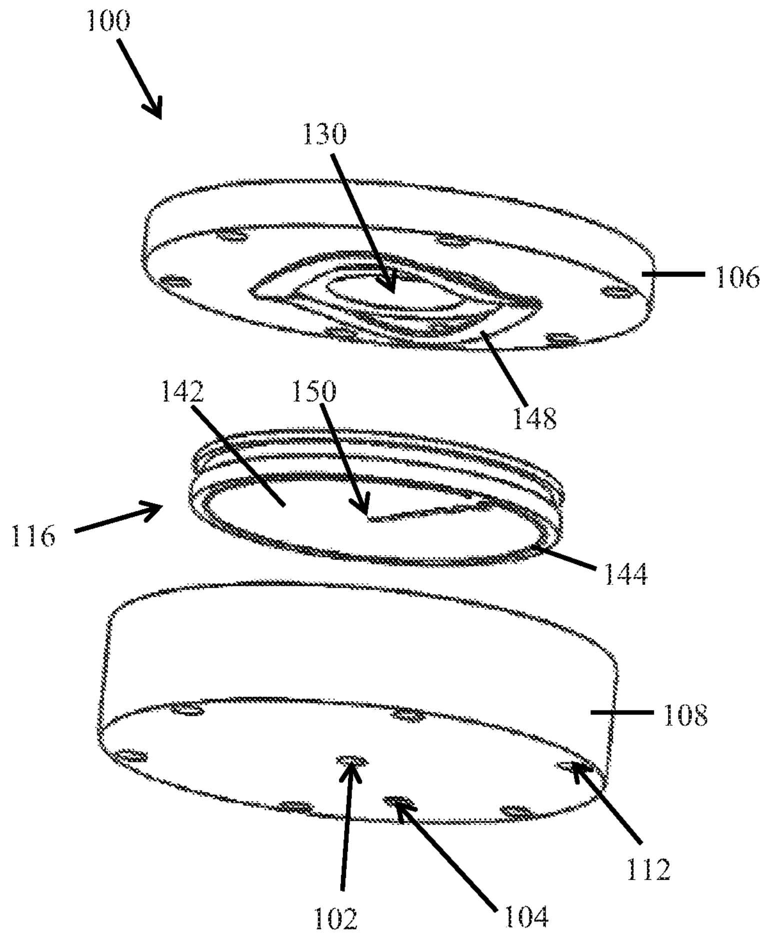
FIG. 4 is a schematic illustration of another exploded view of the dilution device of FIG. 1, according to certain implementations.

FIG. 4 is a schematic illustration of another exploded view of the dilution device 100. The metering disc 116 may be biased toward the second housing component 108. For example, the surface 142 of the metering disc 116 may be biased into engagement with the interior surface 120 (see FIG. 2) of the second housing component 108 to facilitate a fluid-tight seal along the edges of the groove 144. As illustrated in FIG. 4, a biasing element, such as wave spring 148, may bias, such as press, the metering disc 116 against the surface 120 (see FIG. 2) of the second housing component 108 to promote sealing between the surfaces 120, 142. The wave spring 148 may be coupled to the first housing component 106 and may at least partially surround the aperture 130 such that the wave spring 148 does not interfere with adjustment of the metering disc 116 relative to the second housing component 108.

With continued reference to FIG. 4, the inlet 102 and the outlet 104 of the second housing component 108 are in fluid communication with the metering groove 144 on the metering disc 116. For example, the groove 144 may include an inlet portion 150 that is in fluid communication with the inlet 102 and may include an outlet portion 152 that is in fluid communication with the outlet 104 regardless of the angular position of the metering disc 116 relative to the second housing component 108. The groove 144 may be formed in the surface 142 of the metering disc 116 and may extend from a center of the surface 142 to a peripheral area of the surface 142. The inlet portion 150 of the groove 144 may be located at the center of the surface 142, and the outlet portion 152 of the groove 144 may extend along a peripheral area of the surface 142. Rotation of the metering disc 116 relative to the second housing component 108 may change the effective length of the groove 144 through which chemical flows from the inlet 102 to the outlet 104. For example, depending on the angular position of the metering disc 116 relative to the second housing component 108, the outlet 104 may be aligned with different points of the outlet portion 152 of the groove 144, while the inlet 102 may remain aligned with the inlet portion 150 of the groove 144, thus changing the length of the flow path between the inlet 102 and the outlet 104 through the groove 144.

Figure 5:
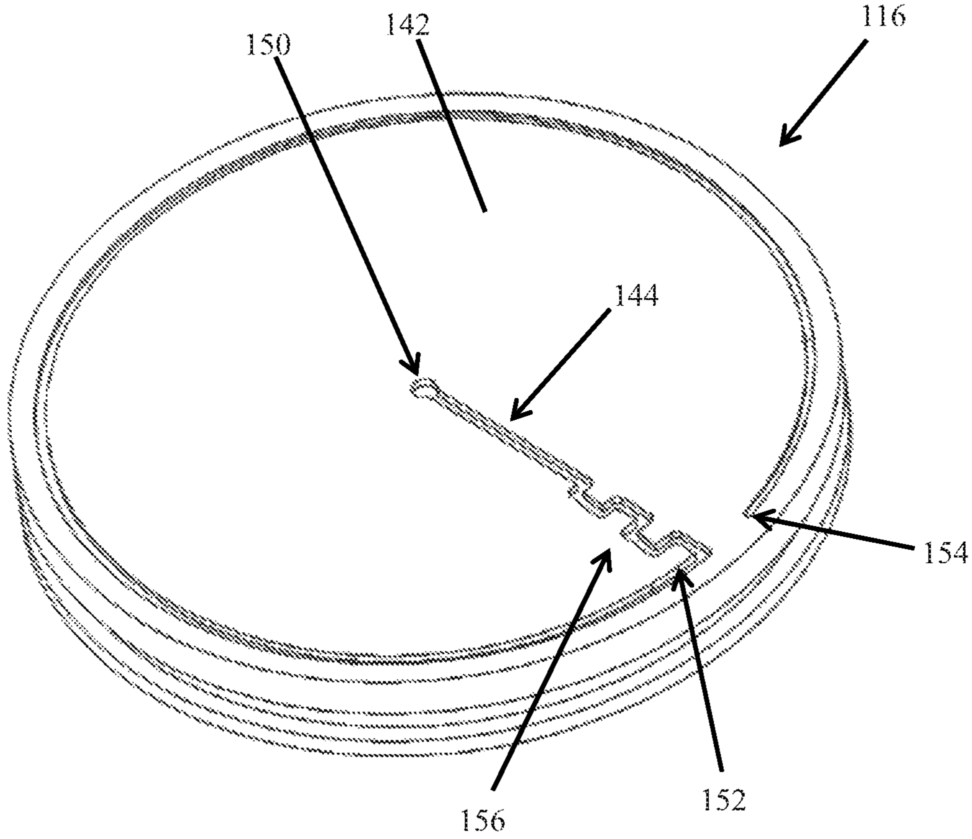
FIG. 5 is a schematic illustration of a metering disc including a metering groove for providing continuous adjustments, according to certain implementations.

FIG. 5 is a schematic illustration of the metering disc 116 with an analog adjustment set-up. The metering groove 144 is configured to provide continuous adjustment of the amount of chemical for mixing with another fluid, such as water. As illustrated in FIG. 5, the groove 144 may extend radially outward from its inlet portion 150 to its outlet portion 152. The outlet portion 152 of the groove 144 may extend along an arcuate path (e.g., circular path) around the peripheral area of the surface 142 of the metering disc 116, and the shortest distance between the inlet portion 150 and the outlet portion 152 may define a radius of curvature of the outlet portion 152. The distance between the inlet portion 150 and the outlet portion 152 of the groove 144 may match the distance between the inlet 102 and the outlet 104 of the second housing component 108 (see, e.g., FIG. 4) such that the inlet 102 is aligned with the inlet portion 150 of the groove 144 and the outlet 104 is aligned with the outlet portion 152 of the groove 144 during rotation of the metering disc 116 relative to the second housing component 108. The groove 144 may originate at the inlet portion 152 and may terminate at an end 154 of the outlet portion 152 to define a maximum effective length of the groove 144.

With continued reference to FIG. 5, the groove 144 may include one or more features that affect the flow rate of chemical through the groove 144 from the inlet 102 to the outlet 104 of the second housing component 108, in addition to being able to vary the effective length of the groove 144. For example, the cross-sectional area of the groove 144 is varied along its length. To vary the cross-sectional area, the width and depth of the groove 144 are varied along the length of the groove 144. The width and depth of the groove 144 may be varied such that rotation of the metering disc 116 in one direction relative to the second housing component 108 causes the chemical flow rate to continually decrease, and rotation of the metering disc 116 in an opposite direction relative to the second housing component 108 causes the chemical flow rate to continually increase. In certain implementations, the depth and the width of the groove 144 are decreased along the length of the groove 144 from the inlet portion 150 to the end 154 of the groove 144. In these implementations, moving the outlet 104 of the second housing component 108 closer to the end 154 along the length of the outlet portion 152 of the groove 144 causes the chemical flow rate to decrease, and moving the outlet 104 away from the end 154 along the length of the outlet portion 152 of the groove 144 causes the chemical flow rate to increase. In one implementation, the groove 144 may be about 0.020 inches wide at its end 154.

Referring still to FIG. 5, the groove 144 may include a tortuous path portion 156 that affects the flow rate of chemical from the inlet 102 to the outlet 104 of the second housing component 108. The tortuous path portion 156 may be located entirely between the inlet portion 150 and the outlet portion 152 and may fluidly couple the inlet portion 150 and the outlet portion 152. For example, as illustrated in FIG. 5, the tortuous path portion 156 may be located along a radial direction extending between the inlet portion 150 located at a center of the surface 142 and the outlet portion 152 located along a peripheral area of the surface 142. The tortuous path portion 156 may restrict the flow of chemical from the inlet portion 150 to the outlet portion 152 of the groove 144, thereby decreasing chemical flow. The tortuous path portion 156 may include twists, turns, and/or other variations in the path of the metering groove 144 to restrict chemical flow from the inlet portion 150 to the outlet portion 152. For example, the tortuous path portion 156 illustrated in FIG. 5 includes eight direction changes (for example, ninety degree bends) in the groove 144 between the inlet portion 160 and the outlet portion 152 that increase flow losses. The number and configuration of direction changes may be varied to achieve desired flow characteristics for a particular implementation.

Figure 6:
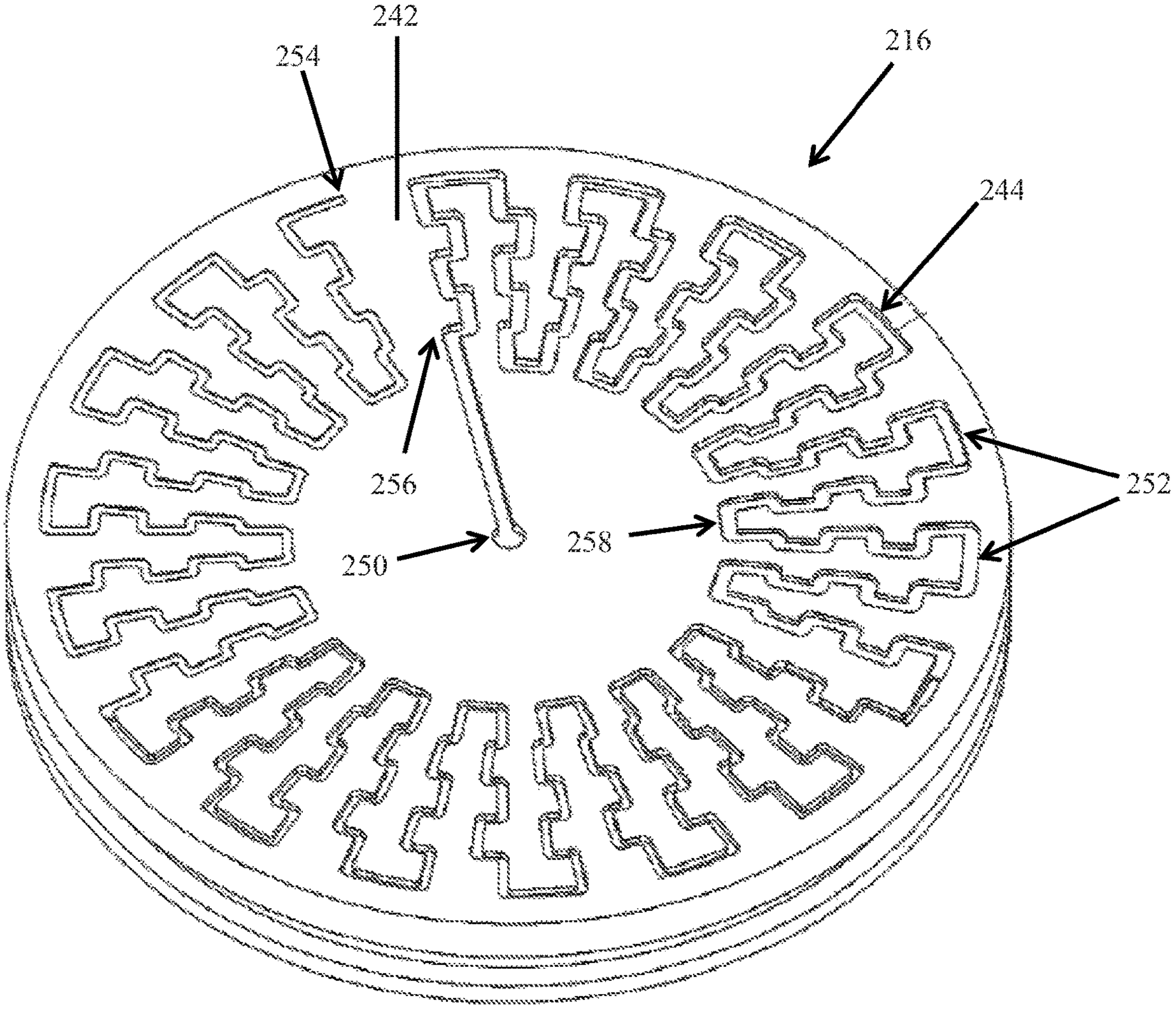
FIG. 6 is a schematic illustration of a metering disc for the dilution device of FIG. 1 that provides discrete adjustments and ultra-low chemical draws, according to certain implementations.

FIG. 6 is a schematic illustration of a metering disc 216 for the dilution device 100 that provides discrete adjustments and ultra-low chemical draws. The metering disc 216 is similar to the metering disc 116, except as described hereinafter. In the following description, features similar to those previously described and illustrated in FIGS. 2-5 are designated with the same reference numbers increased by 100 and redundant description is omitted.

As illustrated in FIG. 6, the metering disc 216 includes a metering groove 244 formed in a flat surface 242. The metering groove 244 originates at an inlet portion 250 and terminates at an end 254. Additional length has been added to the groove 244 as compared to the groove 144 illustrated in FIG. 5, and the additional length provides the capability to further restrict chemical flow from the inlet 102 to the outlet 104 (see FIG. 1). Similar to the groove 144, the depth and width of the metering groove 244 are decreased along the length of the groove 244 to provide the capability of low chemical draw rates. Also similar to the groove 144, the metering groove 244 includes a tortuous path portion 256 located between the inlet portion 250 and the outlet portion 252 to further restrict chemical flow from the inlet 102 to the outlet 104 (see FIG. 1).

Referring still to FIG. 6, to provide the capability of decreased chemical draw rates relative to the metering groove 144, the metering groove 244 includes flow path disruptions (e.g., direction changes such as twists and turns) in the outlet portion 252 of the groove 244, and these additional disruptions further restrict the flow of chemical from the inlet portion 250 toward the end 254 of the groove 244. In the implementation illustrated in FIG. 6, the outlet portion 252 of the groove 244 is divided into multiple segments (hereinafter "outlet portion segments 252") arranged along the same radius of curvature originating at the inlet portion 250, and the outlet portion segments 252 are spaced apart from one another to provide discrete rotational positions of the metering disc 216 relative to the second housing component 108 at which the outlet 104 (see FIG. 1) is aligned with the outlet portion segments 252 to permit chemical flow from the inlet 102 to the outlet 104 (see FIG. 1). In other words, the outlet portion segments 252 are intermittently aligned with the outlet 104 (see FIG. 1) during rotation of the metering disc 216 relative to the second housing component 108 to selectively allow chemical flow from the inlet 102 to the outlet 104 (see FIG. 1).

As illustrated in FIG. 6, tortuous path portions 258 may fluidly couple immediately adjacent outlet portion segments 252 to provide a continuous flow path from the inlet portion 250 to the end 254 of the metering groove 244. The tortuous path portions 258 each may extend radially inward from ends of immediately adjacent outlet portion segments 252 toward the inlet portion 250. The tortuous path portions 258 increase the overall length of the metering groove 244, thereby increasing the flow restriction capability of the groove 244. The tortuous path portions 258 may include twists, turns, and/or other variations in the path of the metering groove 244 to further restrict chemical flow. For example, the tortuous path portions 258 illustrated in FIG. 6 each add twenty direction changes (for example, ninety degree bends) in the groove 244 between immediately adjacent outlet portion segments 252 to increase flow losses, thereby further restricting chemical flow. Moving the outlet 104 of the second housing component 108 (see FIG. 1) closer to the end 154 of the groove 244 (e.g., clockwise in FIG. 6) causes the chemical flow rate to decrease because, for example, the tortuous path portions 258 increase the effective length of the groove 244 coupling the inlet 102 and the outlet 104 and increase flow losses due to flow path direction changes. Alternatively, moving the outlet 104 of the second housing component 108 (see FIG. 1) away from the end 154 of the groove 244 (e.g., counterclockwise in FIG. 6) causes the chemical flow rate to increase because, for example, the effective length and flow losses of the groove 244 are decreased due to the inclusion of fewer tortuous path portions 258 in the flow path between the inlet 102 and outlet 104 (see FIG. 1). The number and configuration of direction changes of the tortuous path portions 258 may be varied to achieve desired flow characteristics for a particular implementation. The geometry of the metering groove 244 illustrated in FIG. 6 achieved ultra-low draw rates in testing, such as producing draw rates as low as 0.2 ml of water per minute.

Figure 7:
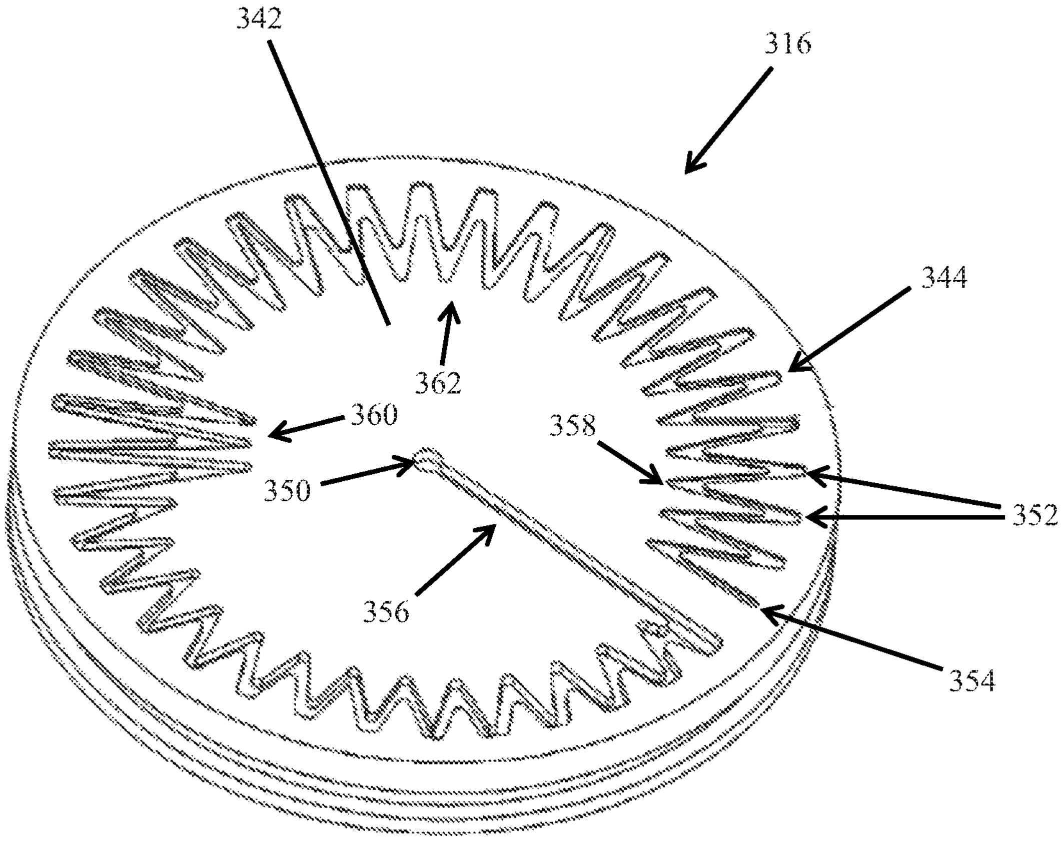
FIG. 7 is a schematic illustration of a metering disc for the dilution device of FIG. 1 with changes to the length and area of a metering groove to affect draw rates, according to certain implementations.

FIG. 7 is a schematic illustration of a metering disc 316 for the dilution device 100 of FIG. 1 and including a metering groove 344 having variable length and area to affect draw rates. The metering disc 316 is similar to the metering disc 216, except as described hereinafter. In the following description, features similar to those previously described and illustrated in FIG. 6 are designated with the same reference numbers increased by 100 and redundant description is omitted.

As illustrated in FIG. 7, the metering disc 316 includes a metering groove 344 formed in a flat surface 342. The metering groove 344 originates at an inlet portion 350 and terminates at an end 354. Similar to the outlet portion 252 of the metering groove 244 illustrated in FIG. 6, the outlet portion 352 of the metering groove 344 is divided into multiple segments (hereinafter "outlet portion segments 352") arranged along the same radius of curvature originating at the inlet portion 250, and the outlet portion segments 352 are spaced apart from one another to provide discrete rotational positions of the metering disc 316 relative to the second housing component 108 at which the outlet 104 (see FIG. 1) is aligned with the outlet portion segments 352 to permit chemical flow from the inlet 102 to the outlet 104 (see FIG. 1). In other words, the outlet portion segments 352 are intermittently aligned with the outlet 104 (see FIG. 1) during rotation of the metering disc 316 relative to the second housing component 108 to selectively allow chemical flow from the inlet 102 to the outlet 104 (see FIG. 1).

Similar to the metering groove 244, the metering groove 344 includes flow path direction changes such as twists and turns in the outlet portion 352 of the groove 344. As illustrated in FIG. 7, tortuous path portions 358 may fluidly couple immediately adjacent outlet portion segments 352 to increase the flow restriction capability of the groove 344 such as by increasing the overall length of the metering groove 344 and by increasing flow losses via changing the flow direction of fluid through the groove 344. The tortuous path portions 358 illustrated in FIG. 7 each add three direction changes (for example, acute bends) in the groove 344 between immediately adjacent outlet portion segments 352 to increase flow losses, thereby restricting chemical flow. The tortuous path portions 358 add fewer direction changes than the tortuous path portions 258 illustrated in FIG. 6 to provide less flow restriction, but the angle of the direction changes in tortuous path portions 358 is more severe than the angle of direction changes in tortuous path portions 258 to provide more flow restriction. The number and configuration of direction changes of the tortuous path portions 358 may be varied to achieve desired flow characteristics for a particular implementation.

In contrast to the metering groove 244, the tortuous path portions 358 may vary in length relative to one another. For example, as illustrated in FIG. 7, the tortuous path portions 358 may gradually increase in length in a radial direction (e.g., direction defined between the inlet portion 350 and respective outlet portion segments 352) as the metering groove 344 approaches its end 354, thereby increasing flow restriction as the outlet 104 (see FIG. 1) is moved toward the end 354 of the groove 344. Additionally or alternatively, as illustrated in FIG. 7, the groove 344 may include select tortuous path portions 360 of greater length than adjacent tortuous path portions 358 to provide a desired flow characteristic at a specific rotational position of the metering disc 316 relative to the second housing component 108 (see FIG. 1).

With continued reference to FIG. 7, the depth and width of the metering groove 344 may be decreased along the length of the groove 344 to provide the capability of low chemical draw rates. However, similar to the select tortuous path portions 360, the metering groove 344 may include select tortuous path portions 362 having greater widths than adjacent tortuous path portions 358 to provide a desired flow characteristic at a specific rotational position of the metering disc 316 relative to the second housing component 108 (see FIG. 1). In contrast to metering grooves 144 and 244 illustrated in FIGS. 5 and 6, respectively, the portion 356 of the metering groove 344 fluidly coupling the inlet portion 350 and the outlet portion 352 extends in a straight line and does not include direction changes such as twists and turns. Different applications might have differing geometries of the metering groove 344 such that the fineness of the adjustment falls in a certain range of adjustment. For example, the geometry of the groove 344 was designed to produce the desired increments in the metering curve illustrated in FIG. 14.

The metering grooves 144, 244, 344 may be shaped to account for different viscosities of chemical. Thicker and colder chemicals flow less, and thus in order to get the same amount of chemical draw the width of the grooves 144, 244, 344 may be increased, which may produce wider spacing between the draw rates. The design of the metering disc 116, 216, 316 may be a compromise for the many viscosities of chemical. For example, as the flows are increased, the adjustment fineness may be decreased (i.e., the incremental increase in chemical from one setting to the next setting is increased) to account for the less precision that is required with higher chemical flows and that as viscosity increases the flow between settings decreases. A higher viscosity chemical typically has a higher setting (i.e., outlet 104 is positioned closer to the inlet portion of the metering groove) than a lower viscosity chemical to achieve the same flow rate.

Figure 8:
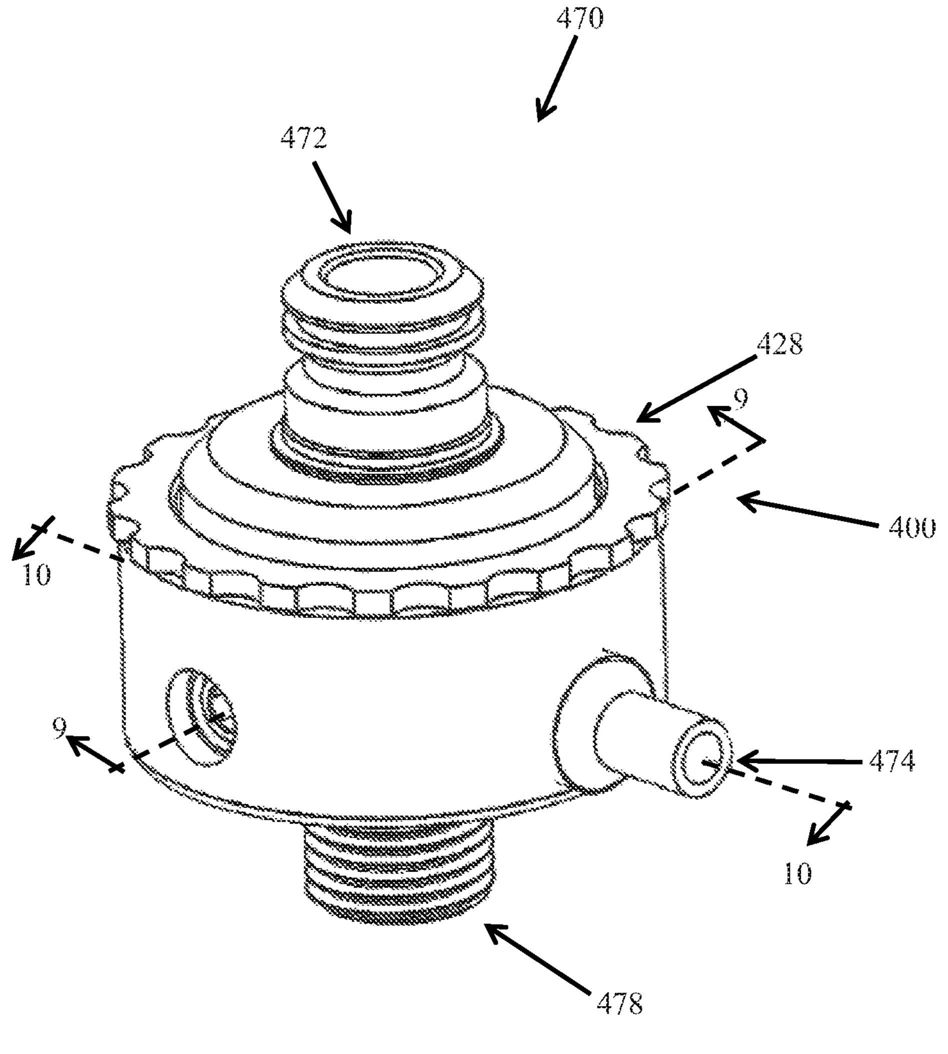
FIG. 8 is a schematic illustration of a dilution system including a dilution device integrated with an eductor, according to certain implementations.

FIG. 8 is a schematic illustration of a dilution device 400 integrated into an eductor 470. In operation, motive fluid such as high pressure water may be received into the eductor 470 through a motive fluid inlet 472 for mixing with a concentrated chemical such as a concentrated car-wash chemical received through a chemical inlet 474 to dilute the concentrated chemical. The motive fluid inlet 472 may be fluidly coupled with a water source via tubing, piping, or the like via a quick connect coupling, for example. The chemical inlet 474 may be fluidly coupled with a chemical source via tubing, piping, or the like via an inlet nipple, for example. The dilution device 400 may be adjustable to regulate the metering of chemical for mixing with the motive fluid to achieve a desired dilution ratio. As illustrated in FIG. 8, the dilution device 400 may include a user engagement feature 428, such as a metering adjustment dial including alternating ridges and grooves for grasping by a user's fingers, to facilitate a user in adjusting the amount of chemical to be mixed with the motive fluid per unit of time. The mixed chemical solution may exit the eductor 470 through an outlet 478, which may be fluidly coupled with an applicator, such as a spray nozzle, via tubing, piping, or the like.

Figure 9:
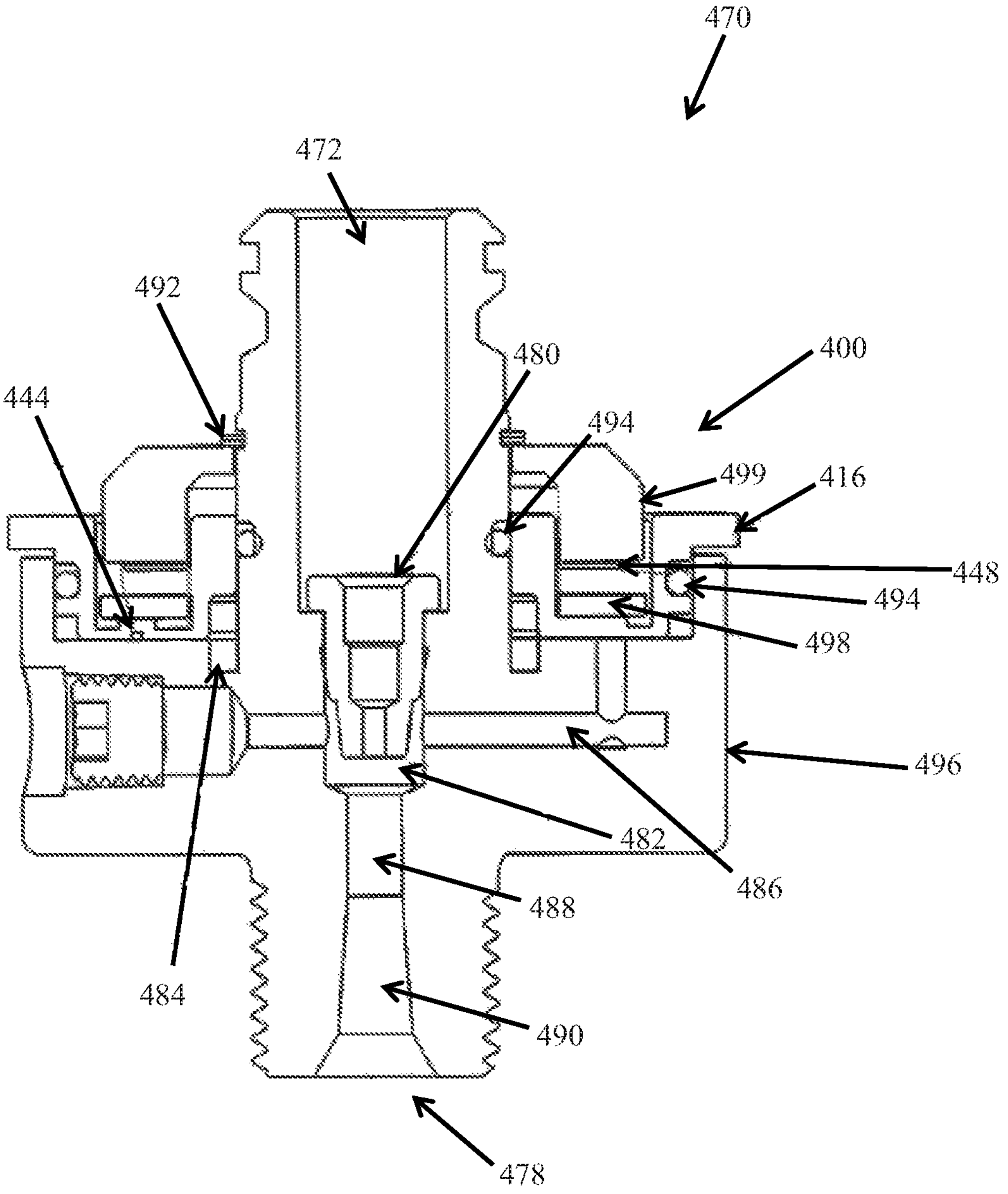
FIG. 9 is a schematic illustration of a cross-section of the dilution system of FIG. 8 taken along line 9-9 of FIG. 8, according to certain implementations.
Figure 10:
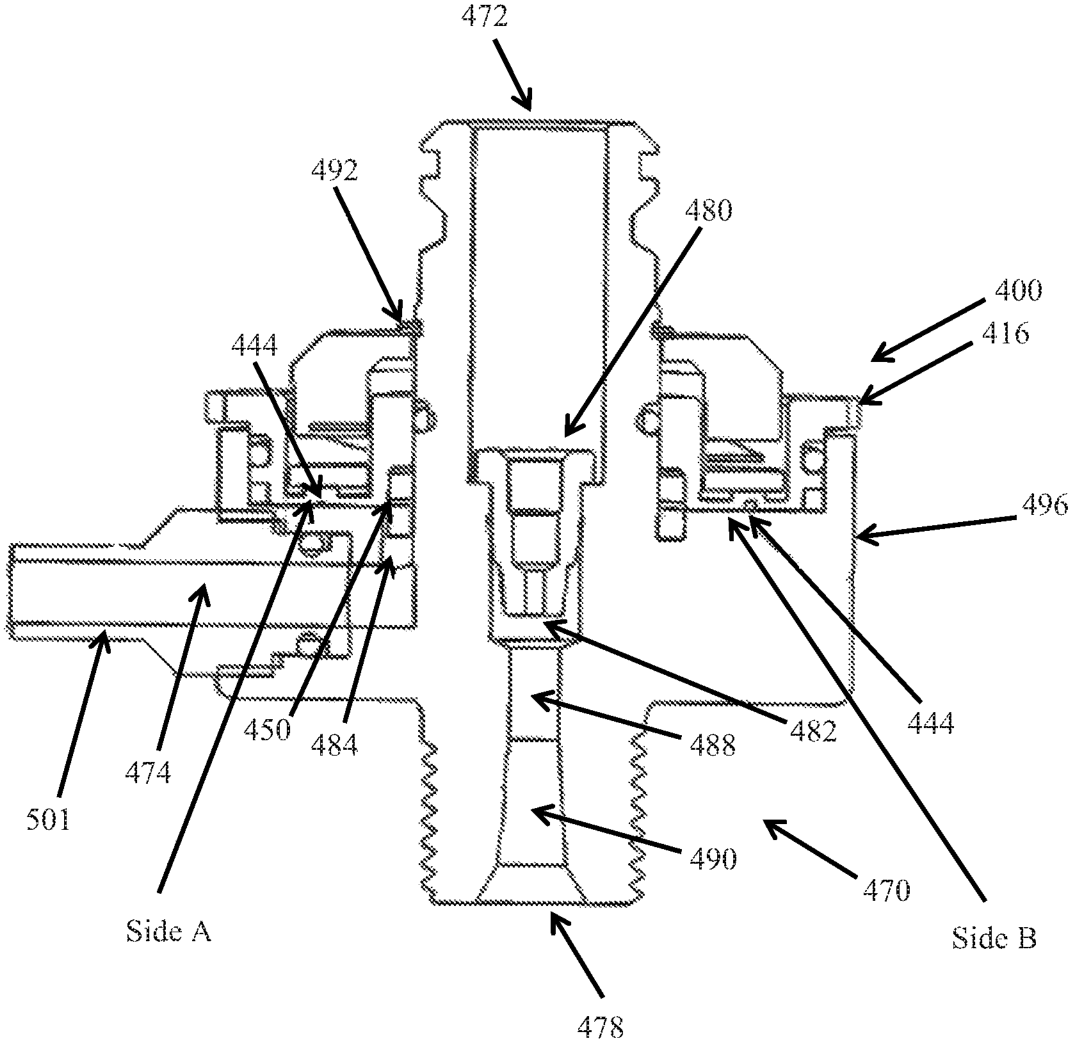
FIG. 10 is a schematic illustration of a cross-section of the dilution system of FIG. 8 taken along line 10-10 of FIG. 8, according to certain implementations.

FIGS. 9 and 10 illustrate cross-sections of the dilution device 400 and the eductor 470 of FIG. 8. In operation, motive fluid travels through the motive fluid inlet 472 and through a nozzle 480 to create a vacuum area 482 downstream of the nozzle 480. Concentrated chemical is drawn through the chemical inlet 474 (see FIG. 9), a chemical inlet channel 484 formed in the eductor 470, a metering groove 444 (e.g., metering groove 144, 244, 344 illustrated in FIGS. 5-7) formed in the dilution device 400, and a chemical outlet channel 486 (see FIG. 9) formed in the eductor 470 into the vacuum area 482 via a suction force generated by motive fluid traveling through the nozzle 480. The concentrated chemical is mixed with the motive fluid in the vacuum area 482 and then the diluted chemical solution exits the eductor 470 through the outlet 478, which may be fluidly coupled with an applicator, such as a spray nozzle, via tubing, piping, or the like. Although not shown in FIG. 10, a replaceable filter element may be located in the chemical inlet 474 to restrict passage of chemical particulates to prevent clogging of the metering groove 444.

The eductor 470 may be configured as a Venturi-style apparatus, such as the Venturi eductor of U.S. Pat. No. 8,807,158. The eductor 470 may define a Venturi throat 488 and a diverging outlet passageway 490 to allow a combination of motive fluid and chemical to be conducted away from the eductor 470 for dispensing. The Venturi throat 488 may define a cross-sectional diameter that is less than the cross-sectional diameter of the outlet passageway 490. As a result, the motive fluid velocity may increase when passing through the Venturi throat 488 and decrease after exiting the Venturi throat 488. Consequently, pressure within the Venturi throat 488 may decrease, forming a first pressure zone upstream of the Venturi throat 488 and a second pressure zone within it. The fluid pressure within the first pressure zone may be higher than that in the second pressure zone. The low pressure within the Venturi throat 488 may create a suction force that draws concentrated chemical into the vacuum area 482, where the chemical mixes with the motive fluid. The concentrated chemical and motive fluid may converge at a perpendicular angle within vacuum area 482 of the eductor 470. The resulting mixture may then pass through the diverging outlet passageway 490 of the eductor 470.

With continued reference to FIGS. 9 and 10, the dilution device 400 may be axially aligned with the eductor 470. The dilution device 400 may define a central aperture for receiving the eductor 470 such that the dilution device 400 is mounted onto the eductor 470. The dilution device 400 may be coupled with the eductor 470 in various manners. In certain implementations, a retaining element, such as a spiral retaining ring 492, may be circumferentially arranged on a portion of the eductor 470 to couple the dilution device 400 to the eductor 470.

Figure 11:
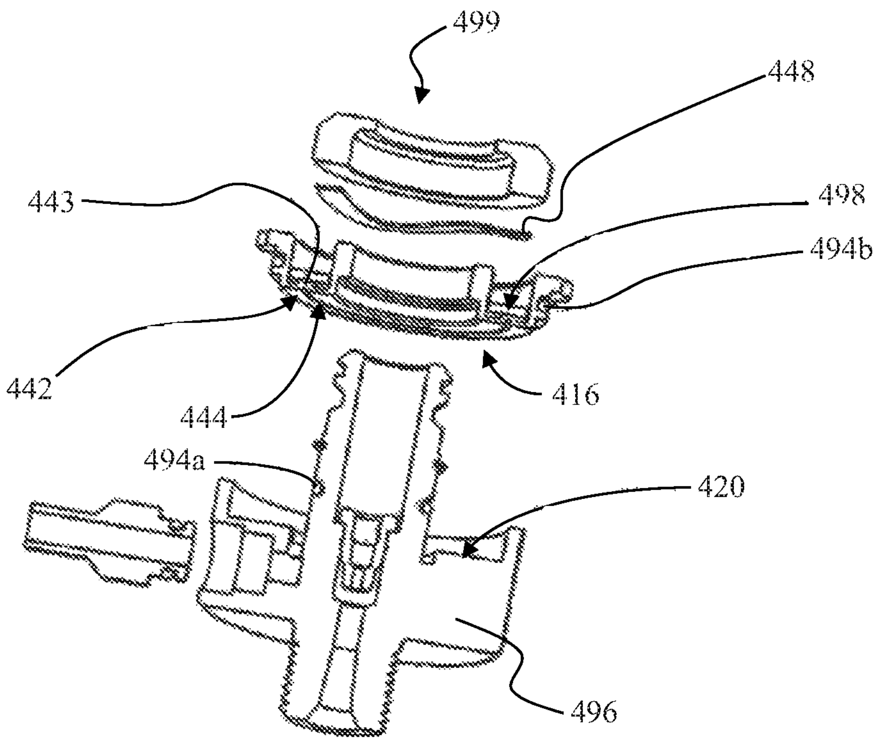
FIG. 11 is a schematic illustration of an exploded view of the dilution system of FIG. 8, according to certain implementations.

The dilution system illustrated in FIGS. 10 and 11 may include one or more sealing elements to restrict leaks between the dilution device 400 and the eductor 470. For example, two sealing elements 494 may prevent leakage of chemical out of the dilution system. The sealing elements 494 may prevent, for example, a vacuum leak in the case the metering disc 416 is not sealed perfectly to a base 496 of the eductor 470. The sealing elements 494 may be O-rings in circumferential engagement with opposing circumferential surfaces of the eductor body 496. One of the sealing elements 494 may be in circumferential engagement with an internal surface of the metering disc 416 and the other of the sealing elements 494 may be in circumferential engagement with an external surface of the metering disc 416. As illustrated in FIG. 9, one of the sealing elements 494 may be circumferentially arranged about a quick connect stem of the eductor 470 to provide a seal between the quick connect stem and the metering disc 416. The other of the sealing elements 494 may be circumferentially arranged about the metering disc 416 to provide a seal between the metering disc 416 and an annular rim of the eductor 470 that confronts the external circumferential surface of the metering disc 416. The number and location of the sealing elements 494 may vary.

As illustrated in FIG. 9, the dilution device may include a pressure plate 498 that provides uniform pressure to the metering disc 416 from a biasing element, such as wave spring 448. The dilution device may include a pressure ring 499 that holds the spring 448 in contact with the pressure plate 498. The pressure ring 499 may be retained in place by the spiral retaining ring 492.

As illustrated in FIG. 10, the eductor 470 may include a removable inlet nipple 501 for connecting to a supply chemical. The inlet nipple 501 may include an inlet filter to prevent clogging the metering groove 444. As illustrated in FIG. 10, the cross-sectional area of the metering groove 444 may change from side A to side B. For example, as shown in FIG. 10, the cross-sectional area of the metering groove 444 may be reduced as the groove 444 extends around the metering disc 444 from side A to side B. To fluidly connect the chemical inlet 474 to the chemical inlet channel 484 that is in fluid communication with the metering groove 444, the chemical inlet channel 484 may be formed as an annulus designed to transfer chemical to the inlet portion 450 of the metering groove 444 of the metering disc 416 around the eductor body 496. The annular shape of the chemical inlet channel 484 may ensure that the inlet portion 450 of the metering groove 444 is in fluid communication with the chemical inlet 474 regardless of the rotational position of the metering disc 416.

FIG. 11 is a schematic illustration of an exploded view of the integrated dilution device and eductor of FIG. 8. As illustrated in FIG. 11, the dilution system can include a pressure plate 498, a wave spring 448, a metering disc 416, and an eductor body 496. The eductor body 496 includes a flat conforming mating surface 420 that confronts a corresponding surface 442 of the metering disc defining the metering groove 444 to form a flow channel therebetween. The eductor body 496 may be made from conformable material, such as HDPE, and the metering disc 416 may be injection molded from various materials, such as HDPE, Kynar, or a similar material. The profile of the metering groove 444 may include a semi-circular cross-sectional shape for injection molding purposes (e.g., mold release and shape control of the groove). To prevent mold sink, the walls around the metering channel may be thin and uniform. Also, the walls around the metering channel may include a stepped type construction to increase the pressure on the interface between the metering disc and the eductor body proximate the metering groove. A small ridge may be molded around the metering groove, and the ridge may protrude from the compliant flat sealing surface of the metering disc and around the edges of the metering groove. The ridges may be designed to deform the soft HDPE body of the eductor and provide a superior seal of the pressure plate to the eductor body around the metering groove, thereby inhibiting leakage in this area to achieve the lowest draw rates. Similarly on the back side of the metering disc where it touches the pressure plate, this area 443 has been slightly raised to contact the pressure plate over a small area above the metering groove 444, causing a slight deformation in the thin walls of the metering disc in this area and helping the ridges around the metering groove to be in full contact with the flat sealing surface of the eductor body. The dilution device may include sealing elements, such as O-rings 1 and 2, 494*a*, 494*b*, to prevent vacuum leaks from escaping around the pressure plate, thereby maintaining the vacuum in the eductor 470 to help draw chemical through the metering groove, reduce chemical leak, and press the pressure plate down (with atmospheric pressure) against the flat sealing surface of the eductor body.

Figure 12:
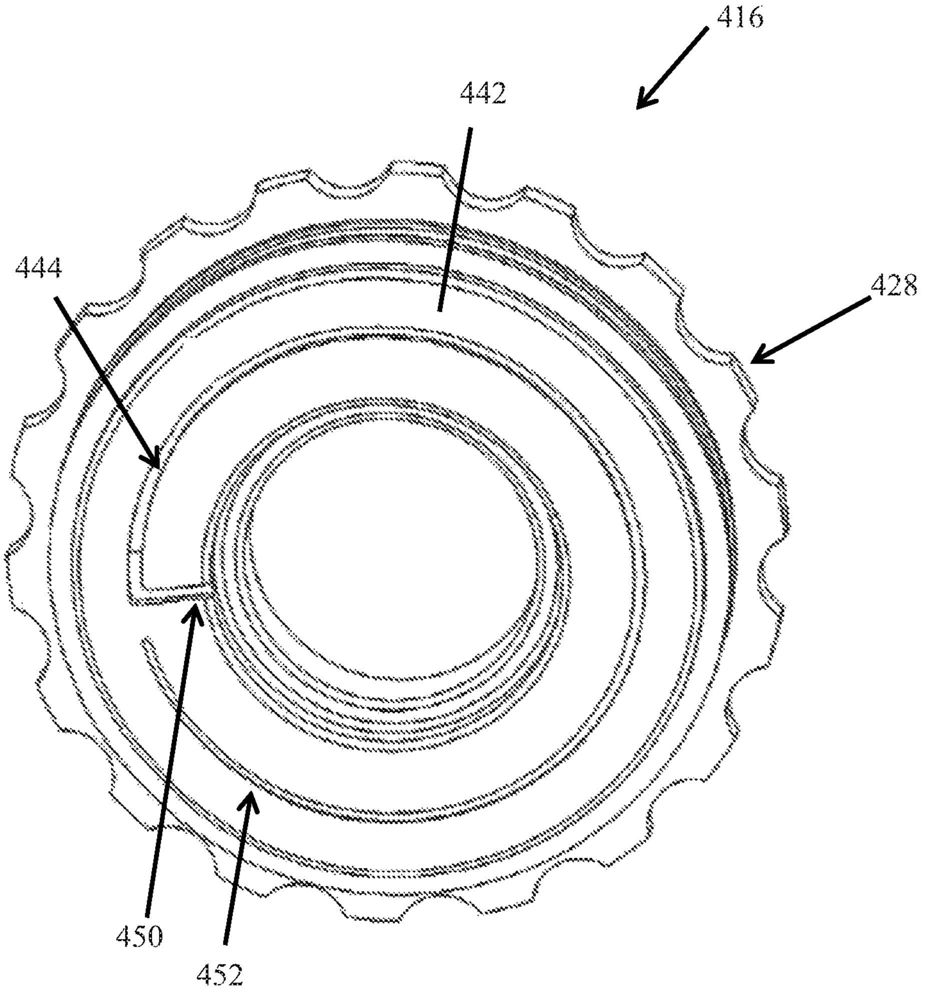
FIG. 12 is a schematic illustration of a metering disc of the dilution system of FIG. 8, according to certain implementations.

FIG. 12 is a schematic illustration of metering disc 416 of the integrated dilution device 400 and eductor 470 of FIG. 8. As illustrated in FIG. 12, the metering disc 416 may include a metering groove 444 formed in a flat sealing surface 442. The metering groove 444 may be in fluid communication with a chemical inlet channel 484 (see FIG. 13), which may include an annular portion to ensure the metering groove 444 remains in fluid communication with the chemical inlet 474 (see FIGS. 9 and 10) regardless of the angular position of the metering disc 416 relative to the eductor body 496. The metering disc 416 may include a user engagement feature 428, as previously discussed.

Figure 13:
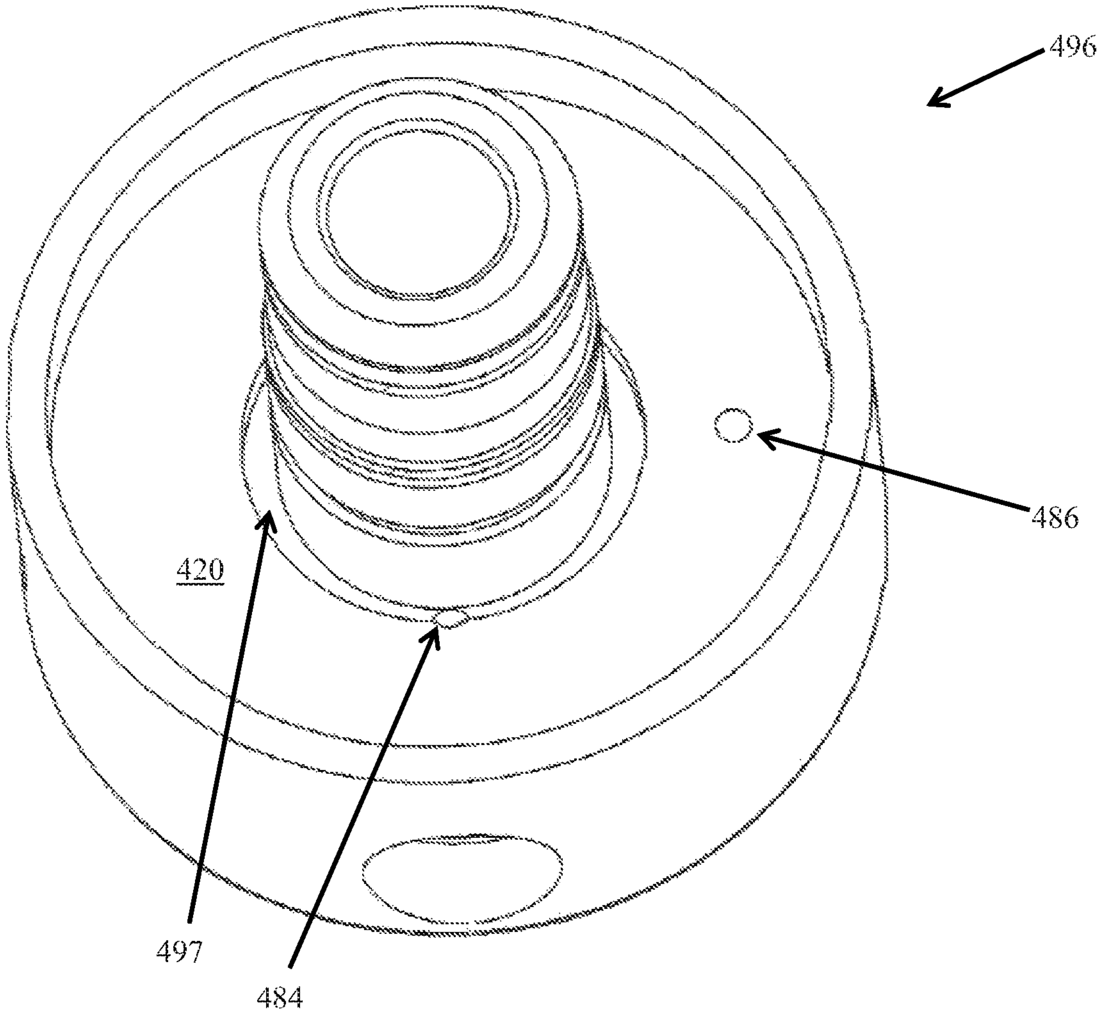
FIG. 13 is a schematic illustration of an eductor body of the dilution system of FIG. 8, according to certain implementations.

FIG. 13 is a schematic illustration of the eductor body 496 of the dilution system of FIG. 8. As illustrated in FIG. 13, the eductor body 496 may include a flat sealing surface 420 that sealingly engages the sealing surface 442 of the metering disc 416 illustrated in FIG. 12. The sealing surface 420 may be softer than the sealing surface 442, such that ridges 146 (see FIG. 3B) extending along edges of the metering groove 444 (see FIG. 12) may depress the sealing surface 420 to form a fluid-tight seal along the edges of the metering groove 444. As illustrated in FIG. 13, the chemical inlet channel 484 is defined in the eductor body 496. The chemical inlet channel 484 fluidly couples the inlet portion 450 of the metering groove 444 (see FIG. 12) with the chemical inlet 474 (see FIG. 10) regardless of the angular position of the metering disc 416 (see FIG. 12) relative to the eductor body 496 via an annular recess 497 formed along an inner periphery of the flat sealing surface 420. As further illustrated in FIG. 13, the chemical outlet channel 486 is defined in the eductor body 496. The chemical outlet channel 486 opens through the flat sealing surface 420 radially outward of the annular recess 497. The chemical outlet channel 486 is in fluid communication with the outlet portion 452 of the metering groove 444 (see FIG. 12). A suction force created in the vacuum area 482 of the eductor body 496 (see FIGS. 9 and 10) via the motive fluid draws the chemical through the metering groove 444 (see FIG. 12) and the chemical outlet channel 486 in the eductor body 496 for mixing with the motive fluid in a cavity defined in the eductor body 496.

Figure 14:
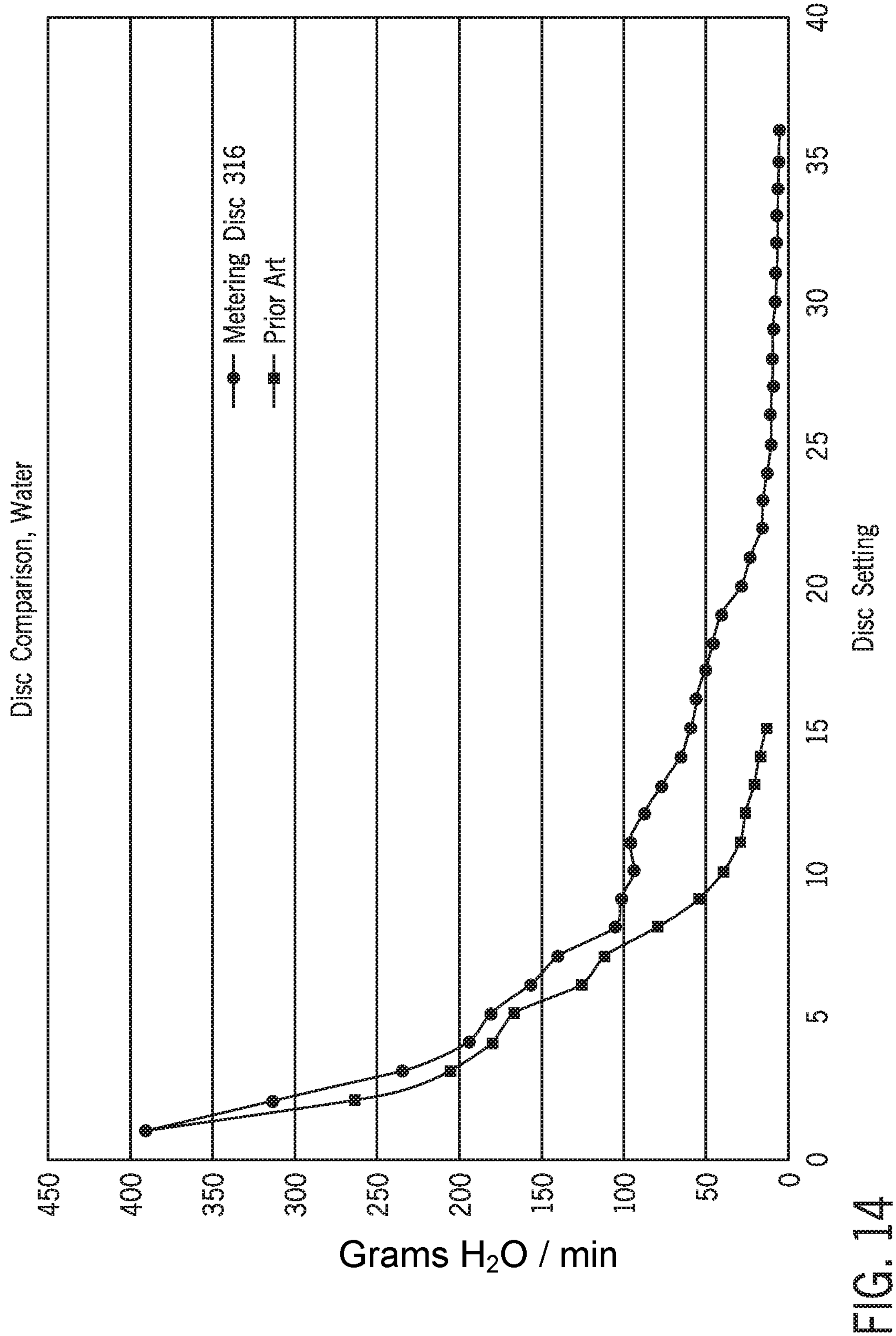
FIG. 14 is a graph comparing performance of the metering disc illustrated in FIG. 7 and a prior art metering orifice, according to certain implementations.

FIG. 14 is a graph comparing performance of the metering disc 316 (see FIG. 7) incorporated into the dilution device 100 (see FIG. 1) and a prior art metering orifice. FIG. 14 illustrates the results of a laboratory test of the metering disc 316 using water drawn by a 3.25 gallons per minute (GPM) eductor operating at 200 psi inlet pressure and 114 degrees Fahrenheit water temperature. The lower line in the graph illustrates the results of prior art metering orifices that are commonly available and in wide use for chemical metering, and the upper line in the graph illustrates the results of the metering disc 316. As illustrated in FIG. 14, the metering disc 316 (upper line) provides more disc settings than the prior art metering orifices over the same range of water flow rate, thereby providing more accurate adjustment of chemical flow over the illustrated range of values.

In certain implementations, the dilution device may be adjustable in an automatic fashion, rather than by human intervention. For example, the dilution device may be automatically adjusted based on a feedback loop signal received from a control system monitoring characteristics of the chemical, the dilution device, and/or the motive fluid. The control system may monitor, for example, the amount of fluid flowing through the dilution device, the concentration of chemical in the emitted fluid mixture downstream of the dilution device, and/or an output of a chemical delivery system. In certain implementations, the control system may monitor the potential of hydrogen (pH) of the diluted fluid, the total dissolved solids (TDS) concentration of the diluted fluid, and/or the conductivity of the diluted fluid. A control system for measuring the amount of fluid flowing through the dilution device may include, for example, a volumetric flow meter, a scale, a mass flow meter, a measurement on a filled volume, and/or a timing of the amount of fluid through an orifice or nozzle. The feedback loop may be managed either electrically or mechanically. In certain implementations, the control system may include a controller, such as a computer, configured to automatically manage the feedback loop.

The control system may adjust the output of the dilution device based on a measured condition. For example, in certain implementations, the dilution ratio downstream of the dilution device is monitored, and the control system automatically adjusts the dilution ratio of the dilution device real time to compensate for dilution ratios downstream of the dilution device that are too rich or too lean relative to a desired ratio. For example, changes in temperature may cause changes in chemical viscosity, which may affect flow of chemical through the dilution device for mixing with the motive fluid, thereby affecting the dilution ratio. The control system may adjust the dilution device to maintain a constant chemical flow rate through the device despite changes in chemical viscosity, thereby maintaining a desired chemical concentration in the emitted fluid mixture.

In another example, when chemical is diluted in water, different water hardness levels may require more or less chemical in solution to effectively clean a surface because many chemicals react with the hardness in the water, resulting in a less potent solution. Water hardness may change frequently for a given water supply, such as municipality water in a given geographic location. In response to an increase in the hardness of the water, the control system may increase the amount of chemical added to the water to compensate for some chemical reacting with the hard water.

In a further example, environmental conditions may affect the chemical levels. For example, the control system may adjust the amount of chemical delivered to the motive fluid based on environmental conditions. In certain implementations, the control system may adjust the amount of chemical based on the condition of the targeted surface, such as the amount of soil on the surface, the type of soil on the surface, and/or the temperature of the surface. The control system may adjust the amount of chemical for a surface that is particularly soiled, has a particular type of soil upon it, and/or is hot, among other environmental conditions. By adjusting the amount of chemical based on environmental conditions, the control system may control the dilution device to create a diluted chemical concentration for effectively cleaning the targeted surface.

Figure 15:
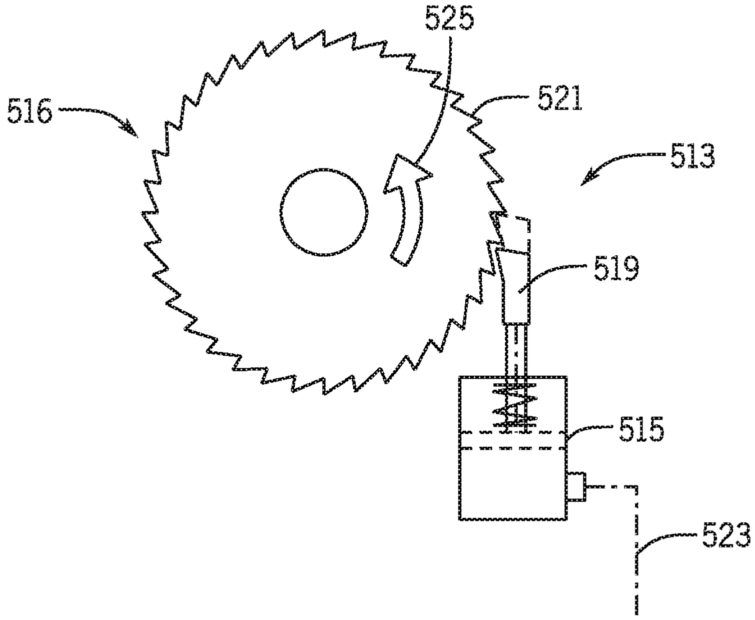
FIG. 15 is a schematic illustration of a control system for automatically adjusting the dilution ratio of a dilution device, according to certain implementations.

FIG. 15 is a schematic illustration of a control system for automatically adjusting the dilution ratio of a dilution device, such as the dilution devices previously described. As illustrated in FIG. 15, the control system 513 includes an actuator 515 for selectively rotating a metering disc 516, which may be configured and may function similar to the previously described metering discs 116, 216, 316, 416. The actuator 515 may be coupled with a pawl 519 and may move (e.g., cycle) the pawl 519 to selectively engage and rotate the metering disc 516 to adjust the flow of chemical through the dilution device. In FIG. 15, an initial position of the pawl 519 is illustrated in solid line and an extended position of the pawl 519 is illustrated in dashed line, thereby illustrating the stroke of the pawl 519 that causes the metering disc 516 to rotate accordingly. The actuator 515 may be an electric solenoid, air cylinder, or other actuator capable of moving the pawl 519 to selectively engage and rotate the metering disc 516. The actuator 515 may receive an input signal 523, such as an electrical or air signal, that causes the actuator 515 to move (e.g., cycle) the pawl 519 and rotate the metering disc 516 to adjust the dilution ratio. The input signal 523 may be based on monitored conditions as previously discussed, and the actuator 515 may cycle the pawl 519 based on the monitored conditions to rotate the metering disc 516 to its desired setting.

The metering disc 516 may include an engagement feature, such as teeth 521, for engagement by the pawl 519. Each tooth 521 of the metering disc 516 may correspond to a different chemical setting (e.g., a different flow path between an inlet and outlet of the dilution device), thereby providing different dilution ratios depending on the rotational position of the metering disc 516. The metering disc 516 may include various numbers of teeth 521 depending on the desired number of settings.

Figure 16:
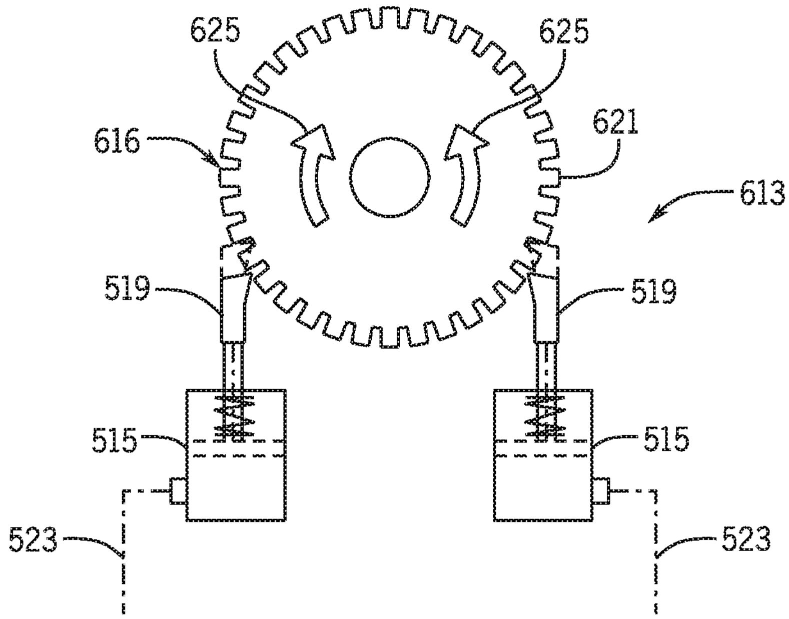
FIG. 16 is a schematic illustration of another control system for automatically adjusting the dilution ratio of a dilution device, according to certain implementations.

The control system 513 illustrated in FIG. 15 is configured to advance the metering disc 516 in one rotational direction as represented by arrow 525, and thus the flow rate of chemical is incrementally adjusted from one setting to an adjacent setting until the desired setting is achieved. For example, for a metering disc including thirty-two settings (e.g., thirty-two teeth) and a pawl configured to incrementally advance the metering disc to a next larger setting, the metering disc would have to be advanced thirty-one times to go to the next smaller setting. FIG. 16 is a schematic illustration of another control system 613 similar to the control system 513 illustrated in FIG. 15, but, in contrast to the control system 513 illustrated in FIG. 15, the control system 613 illustrated in FIG. 16 is configured to rotate a metering disc 616 (such as metering discs 116, 216, 316, 416) in either direction, as represented by arrows 625. The control system 613 may include two actuators 515 and pawls 519, which may be the same or substantially the same as those used in control system 513. The actuators 515 and pawls 519 in control system 613 may be positioned to engage opposite faces of the teeth 621 of the metering disc 616 relative to each other, thereby rotating the metering disc 616 in opposite directions when the respective pawls 519 are actuated. The respective actuators 515 may receive respective input signals 523 to control movement of the pawls 519 and thus rotation of the metering disc 616. The metering disc 616 may include teeth 621 configured such that the metering disc 616 can be advanced in either direction. In other words, the metering disc 616 may be rotated either clockwise or counterclockwise to achieve a desired setting. The teeth 621 may be symmetrical to facilitate engagement by either of the pawls 519, whereas the teeth 521 in FIG. 15 may be asymmetric.

Figure 17:
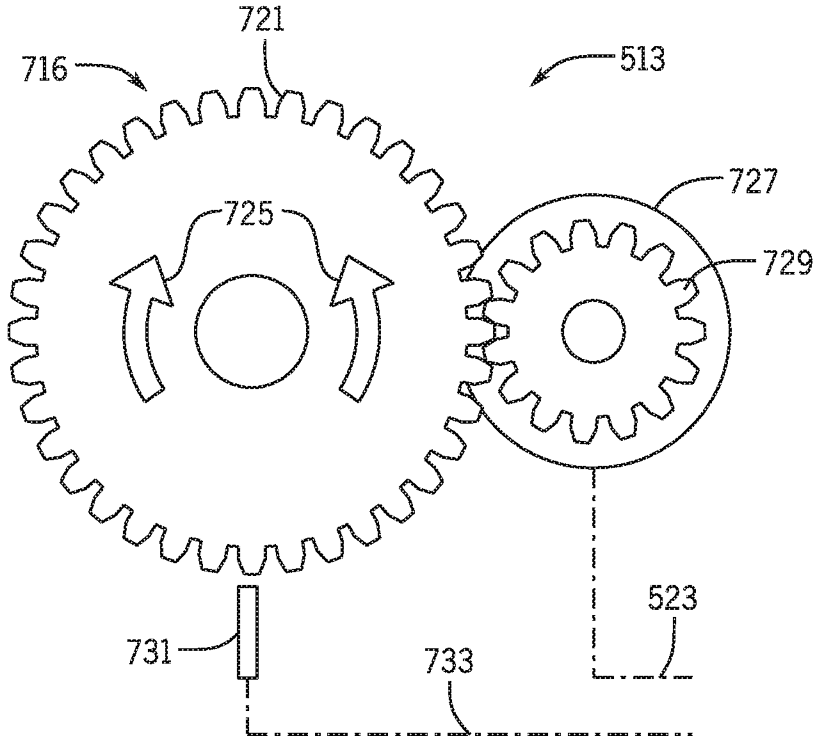
FIG. 17 is a schematic illustration of a yet another control system for automatically adjusting the dilution ratio of a dilution device, according to certain implementations.

FIG. 17 is a schematic illustration of a control system 713 with continuous adjustment, in contrast to the control systems 513, 613 illustrated in FIGS. 15 and 16 with discrete adjustment intervals. As illustrated in FIG. 17, the metering disc 716 (which may be configured and may function similar to the previously described metering discs 116, 216, 316, 416) is adjustable in an analog setting so that any rotational position (and thus chemical flow value) may be obtained, rather than the step by step adjustment of control systems 513 and 613. As illustrated in FIG. 17, the metering disc 716 may be driven by an actuator, such as motor 727, with a gear 729 that engages teeth 721 on the metering disc 716. The motor 727 can rotate the metering disc 716 in either direction, as represented by arrows 725 in FIG. 17, via the gear 729 to adjust the rotational position of the metering disc 716 to the desired setting. The motor 727 may receive the input signal 523 to cause the motor 727 to rotate the gear 729, thereby rotating the metering disc 716 to adjust the dilution ratio based on, for example, the monitored conditions previously discussed.

As illustrated in FIG. 17, the control system 713 may include a locating sensor 731 to determine the rotational position of the metering disc 716. The locating sensor 731 may be a proximity switch that counts the number of teeth 721 on the metering disc 716 as respective teeth 721 pass by the sensor 731, and therefore the control system 713 can determine the location of the metering disc 716. The locating sensor 731 may be an optical encoder, a variable resistor, and/or other components capable of determining or facilitating determination of the location of the metering disc 716. Although not illustrated in FIGS. 15 and 16, the locating sensor 731 may be added to the control systems 513, 613.

The locating sensor 731 may be in communication with a computer via signal 733 to ensure the metering disc 716 is in its desired location. Adjustment of the rotational position of the metering disc 716 may be in response to a feedback loop or in response to known changing conditions. For example, the actuator associated with the metering disc 716 may be used to move the disc 716 until locating sensor 731 indicates the metering disc 716 is at a predetermined positon. This repositioning may be performed on a predetermined schedule or when an external condition, such as temperature, changes. For example, when a dirty cleaning surface is encountered, the position of the disc 716 may be set to deliver a greater amount of chemical. Another example is the disc 716 may be moved to deliver less chemical on a timed schedule in order to change the chemical delivery based on known conditions such as excessive bugs on the front of a car and fewer on the rear of the car. Thus, more chemical may be applied to areas of expected greater soil.

Figure 18:
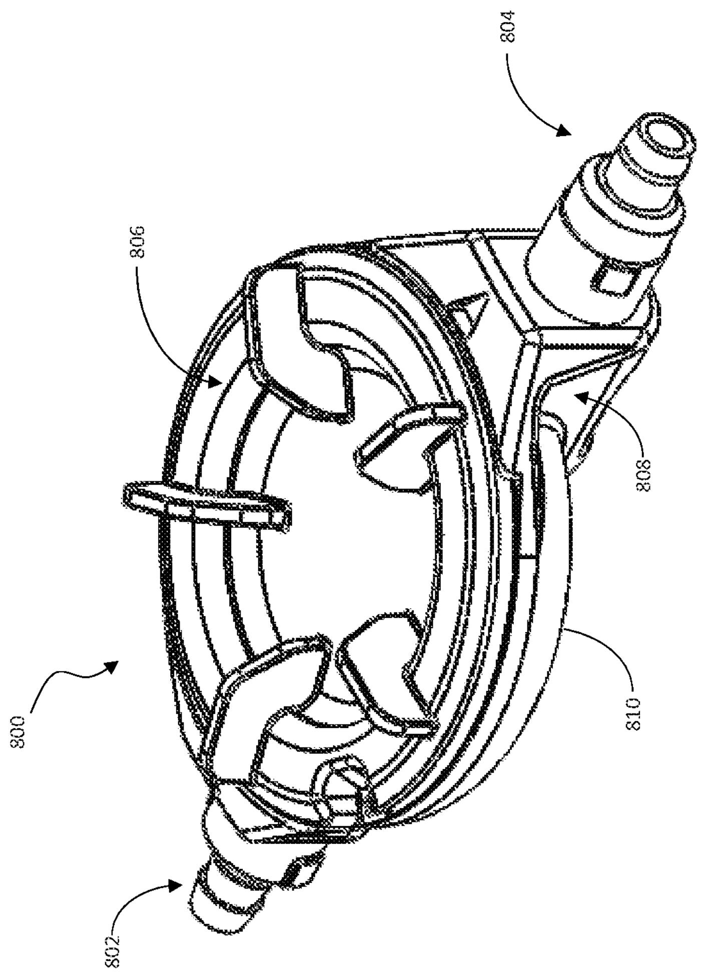
FIG. 18 is a schematic illustration of another dilution device, according to certain implementations.

FIG. 18 is a schematic illustration of another dilution device 800 configured for dispensing fluid. In various implementations, the dilution device 800 may comprise a metering device configured for dispensing car wash solution. As shown in FIG. 18, the dilution devices disclosed herein may be configured to input and output fluids from multiple directions relative to an internal metering component. As a result, the devices can be mounted in various positions and thus compatible with various dispensing systems. The dilution device 800 includes an inlet nozzle 802 and an outlet nozzle 804. The inlet nozzle 802 may be in fluid communication with a chemical, which may be stored in a chemical container at atmospheric pressure. The outlet nozzle 804 may be in fluid communication with the inlet nozzle 802 via a flow channel. The outlet nozzle 804 also may be in fluid communication with a chemical mixing device, such as an eductor. For example, the outlet nozzle 804 may be fluidly coupled with a chemical inlet of an eductor. In some examples, the connection between the eductor and outlet nozzle 804 may be of a barbed hose type, quick connect, or other means. In certain implementations, the chemical inlet of the eductor typically draws about 25 to 28 inches of mercury (inHg) of vacuum with an inlet water pressure of about 200 pound force per square inch (psi). The difference between the vacuum in the eductor and the atmospheric pressure at the inlet nozzle 802 creates a pressure differential that draws chemical through the dilution device 800.

As illustrated in FIG. 18, the dilution device 800 may include a first housing component 806 and a second housing component 808. The first housing component 806 may function as a cover for the second housing component 808. In certain implementations, the first housing component 806 may be formed as a rounded plate or molded component. Furthermore, the inlet nozzle 802 and the outlet nozzle 804 may be coupled with a chemical container and an eductor, respectively, via a flexible hose in some examples, such as the flexible hose 811 shown partially inserted into the inlet nozzle 802 in FIG. 19. The connections may be provided as an integral part of the dilution device 800 joined by mechanical means of threading, welding, or other adhesion. The outer surface 810 may be planar (i.e., flat) or rounded, and may be formed of machined polyethylene in some examples. The outer surface 810 may also be formed to provide attachment to an integrated panel system for storage and removal for adjustment. In the example shown, the inlet nozzle 802 and the outlet nozzle 804 are positioned on opposite surfaces around the circumference of the device 800, such that the nozzles protrude radially outward and away from each other along approximately the same lateral plane.

Figure 19:
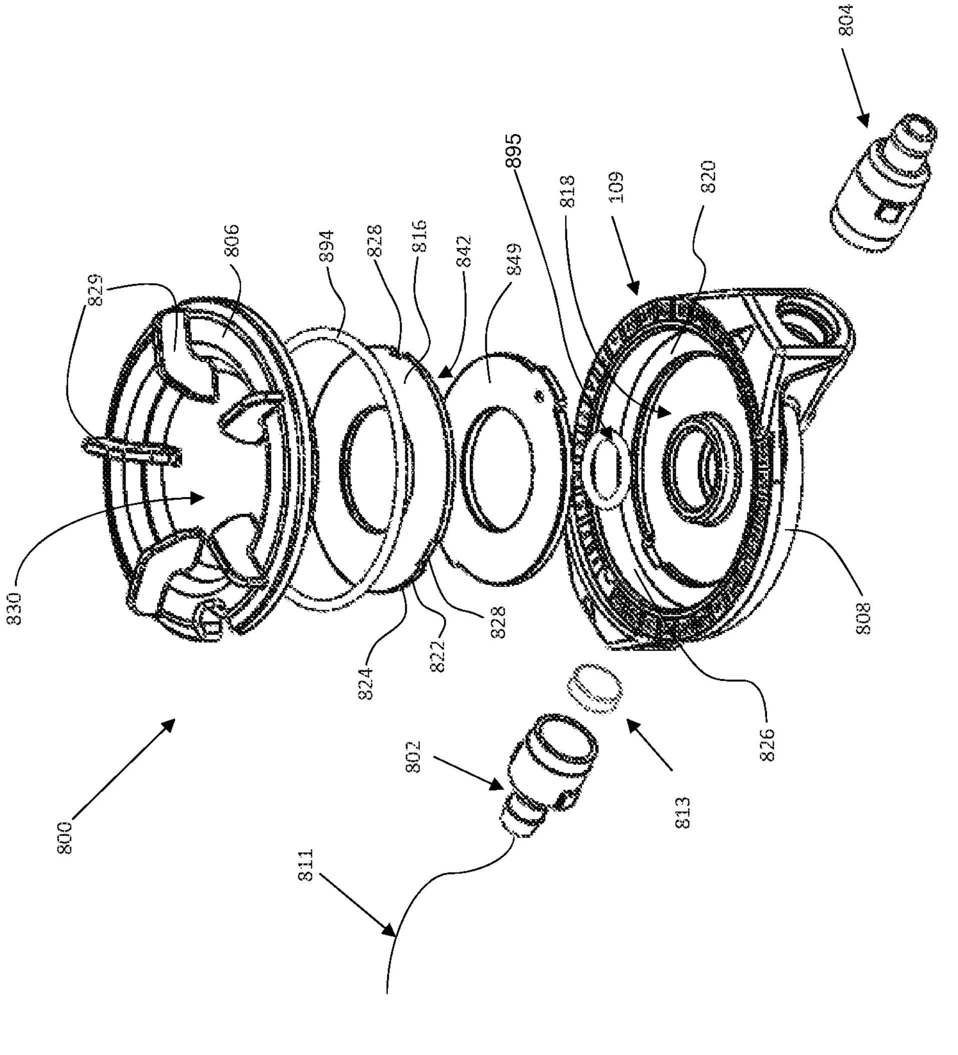
FIG. 19 is a schematic illustration of an exploded view of the dilution device of FIG. 18, according to certain implementations.

FIG. 19 is a schematic illustration of an exploded view of the dilution device 800. As shown, the dilution device 800 can include a metering component, such as a metering disc 816. The metering disc 816 may be received in a cavity 818 formed at least partially in the second housing component 808. In a similar fashion, the metering disc 816 may be received in a cavity formed in the first housing component 806. The inlet nozzle 802 and the outlet nozzle 804 may open through an interior surface 820 of the second housing component 808 into the cavity 818. The interior surface 820 may be planar (i.e., flat) in various embodiments. The metering disc 816 may sealingly engage the second housing component 808 to maintain fluid flow between the inlet nozzle 802 and the outlet nozzle 804 with little to no leaking. For example, a sealing element 894 may be retained in a groove 822 formed in a circumferential surface 824 of the metering disc 816, such that the sealing element 894 may engage a corresponding circumferential surface 826 of the second housing component 808 to form a fluid-tight seal between the metering disc 816 and the second housing component 808. A second sealing element 895, e.g., O-ring, may also be included to seal the cavity 818. The circumferential surface 826 may extend orthogonally to the interior surface 820. The interior surface 820 may form a fluid-tight seal with a corresponding surface of the metering disc 816, as described in more detail below. In some embodiments, the first housing component 806 and the second housing component 808 may also be coupled together by means of a snap fit or other mechanic retention. As further shown, a replaceable filter element 813 may be located in or coupled with the first nozzle 802 to restrict passage of chemical particulates and prevent clogging of the metering groove, e.g., metering groove 844 of FIG. 20.

The metering disc 816 may be rotatable relative to the first housing component 806, the second housing component 808, or both. As illustrated in FIG. 19, the device 800 may include at least one adjustment feature configured to facilitate rotating the metering disc 816 relative to the second housing component 808. For example, a user engagement feature 828, such as the illustrated adjustment slots, may be accessible through an aperture 830 formed through the first housing component 806. One or more user actuation features, e.g., interlocking tabs 829, may also be incorporated into the first housing component 806, and may be manipulable via manual actuation. To adjust the position of the metering disc 816, the tabs 829 can be engaged with the corresponding slots 828 and rotated, thereby modifying the outlet portion segment through which fluid is dispelled from the metering groove (see e.g., metering groove 844 in FIG. 20). Via such adjustment features, the metering disc 816 may provide continuous or discrete adjustment relative to the second housing component 808 depending on, for example, the particular geometry of the metering groove defined by the metering disc 816. Additional user engagement features and user actuation features may be included in additional embodiments. For example, a user actuation feature may include a pin configured for insertion into a user engagement feature comprised of a complementary slot. Alternatively, a user engagement/actuation feature may comprise a lockable push-button/aperture combination.

The metering disc 816 may be biased toward the second housing component 808. For example, a surface 842 of the metering disc 816 may be biased into engagement with the interior surface 820 of the second housing component 808 to facilitate a fluid-tight seal between the two components. As further illustrated in FIG. 19, a biasing element 849 may bias, e.g., press, the metering disc 816 between the surface 820 of the second housing component 808 and an inner surface of the first housing component 806 to promote sealing between the surfaces 820, 842. The biasing element 849 may be coupled to the second housing component 808 and can at least partially surround the aperture 830 such that the biasing element 849 does not interfere with adjustment of the metering disc 816 relative to the second housing component 808. Similarly, an elastomer material, such as a closed cell foam, may be used to bias the metering disc 816 toward the second housing component 808. The biasing element 849 may engage with the second housing component 808 to ensure fluid flow through the metering disc 816 is directed as needed from the inlet nozzle 802 to the outlet nozzle 804.

Figure 20:
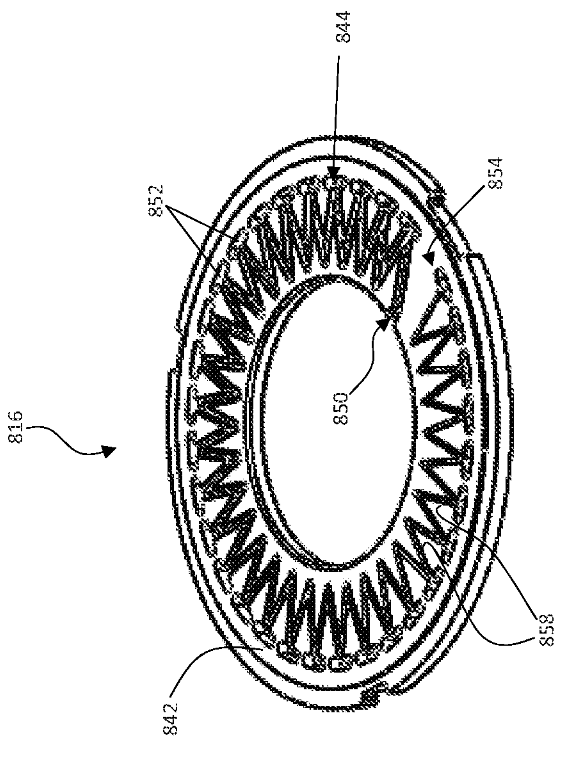
FIG. 20 is a schematic illustration of a metering disc including a metering groove for providing flow rate adjustments, according to certain implementations.

FIG. 20 shows the metering disc 816, including the metering groove featured in this specific example. As shown, the metering disc 816 defines a metering groove 844 that originates at an inlet portion 850 and terminates at an end portion 854. The metering disc 816 also defines an enlarged outlet interface on surface 842 at the outlet portion segments 852, which may allow for increased range in adjustment of the first housing component 806 to achieve accurate output flow at specifically desired rates. The metering groove 844 defines a tortuous portion 858 fluidly coupling the inlet portion 850 and the outlet portion segments 852. As shown, the tortuous portion 858 extends in straight lines that do not include arcuate direction changes, e.g., twists and turns; however, different applications can have differing geometries of the metering groove 844.

Figure 21:
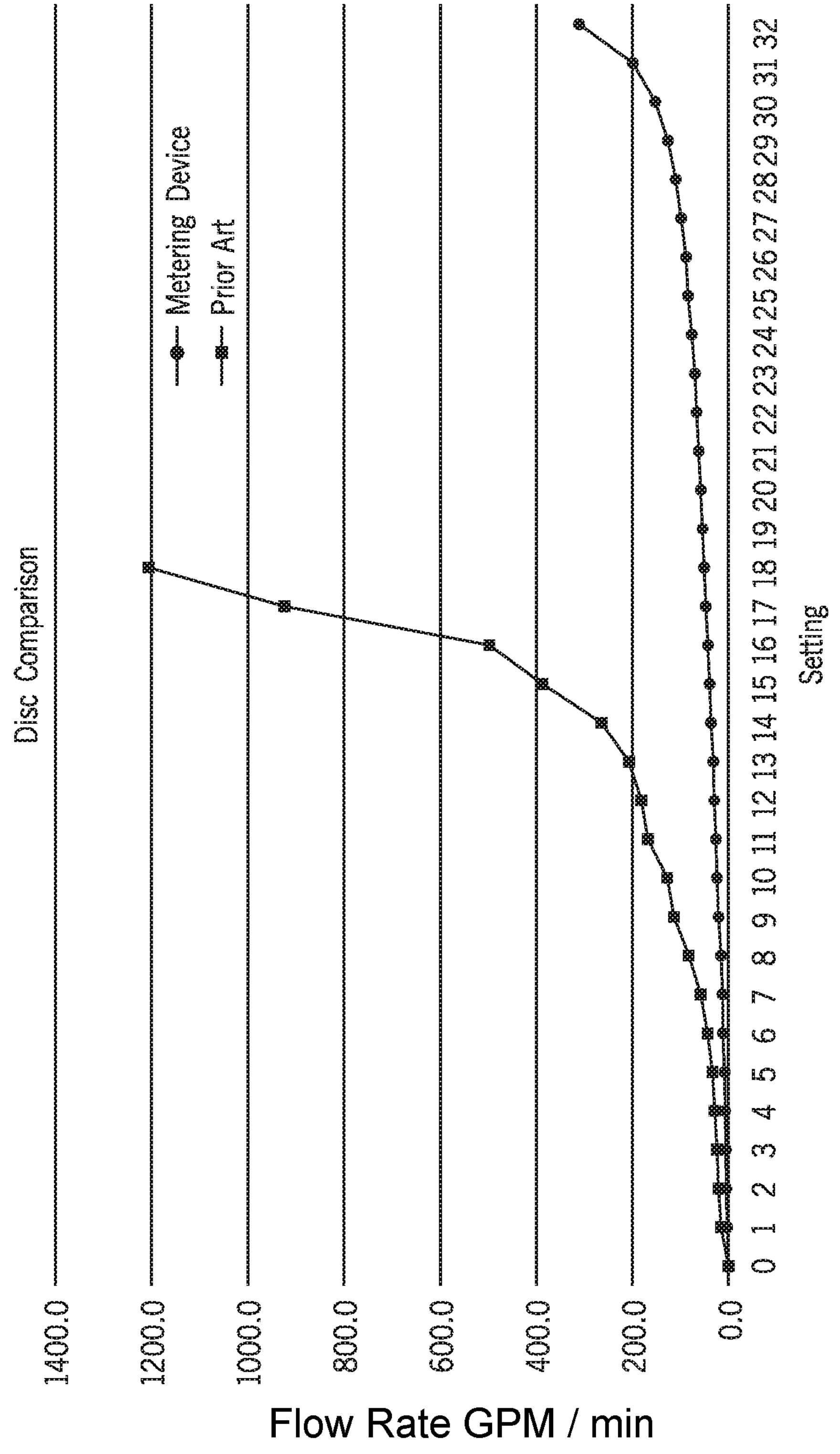
FIG. 21 is a graph comparing performance of the metering disc illustrated in FIG. 20 and a preexisting metering orifice, according to certain implementations.

FIG. 21 is a graph comparing performance of the metering disc 816 incorporated into the dilution device 800 and a preexisting metering orifice. The graph illustrates the results of a laboratory test of the metering disc 816 using water drawn by a 3.25 gallons per minute (GPM) eductor operating at 200 psi inlet pressure and 78 degrees Fahrenheit water temperature. The upper line in the graph illustrates the results of prior art metering orifices that are commonly available and used for chemical metering, and the lower line in the graph illustrates the results of the metering disc 816. As illustrated in FIG. 21, the metering disc 816 disclosed herein provides more disc settings than preexisting metering orifices over the same range of water flow rates, thereby providing more accurate, refined adjustment of chemical flow over the illustrated range of values.

Various components of the dilution system may be integrally constructed. The integral construction may, for instance, be by molding (e.g., injection molding) a chemically inert polymer such as HDPE, PTFE or PVDF. At least some components of the dilution system may be constructed of inert polymers, while others may be constructed of metal, such as spring clips, helical springs, and inlet connectors. To decrease the cost of the parts and/or improve chemical resistance, components of the dilution system may be molded from a plastic material. These components may additionally or alternatively be machined or additive manufacturing may be used for their construction. The dilution devices and system described herein may be particularly useful in the car wash and industrial cleaning industries. The dilution devices and systems described herein may be applicable to other industries as well. For example, changing the dilution of drugs delivered to a patient on a schedule that keeps a constant blood concentration level.

Although certain embodiments of the present disclosure are described herein with reference to the examples in the accompanying figures, it would be apparent to those skilled in the art that several modifications to the described embodiments, as well as other embodiments of the present invention are possible without departing from the spirit and scope of the present disclosure.

What is claimed is:

1. A dilution device, comprising:

a first component comprising a metering disc having a cross-sectional thickness, the metering disc defining a single metering groove having an inlet portion and an outlet portion, the groove formed in a surface of the metering disc and having a depth that is less than the cross-sectional thickness of the metering disc; and a second component comprising a first housing component coupled with a second housing component, wherein the first and second housing components define an interior of the second component enclosing the first component, the first housing component defining an aperture and the second housing component defining an inlet in fluid communication with the inlet portion of the first component and an outlet in fluid communication with the outlet portion of the first component, the inlet and the outlet each comprising a through-hole extending through the second housing component from the interior to an exterior of the second component, the inlet configured for receiving a chemical and the outlet configured for coupling with an eductor having a motive fluid passage through the eductor;

wherein:

relative rotation between the first component and the second component causes relative movement between the outlet and the outlet portion that changes an effective length of the groove fluidly coupling the inlet and the outlet of the second component; and the cross-sectional area of the groove varies along a length of the groove to provide different flow restriction depending on the effective length of the groove.

2. The dilution device of claim 1, wherein the depth and the width of the groove vary along the length of the groove.

3. The dilution device of claim 1, wherein the groove travels along a tortuous path with multiple direction changes.

4. The dilution device of claim 1, wherein the relative rotation between the first component and the second component is automatically controlled without user intervention.

5. The dilution device of claim 1, further comprising an adjustment feature configured to cause the relative rotation between the first component and the second component responsive to user manipulation.

6. The dilution device of claim 5, wherein the adjustment feature comprises a slot.

7. The dilution device of claim 1, further comprising a biasing element configured to bias the first component against an internal surface of the second component.

8. The dilution device of claim 7, wherein the biasing element comprises a wave spring.

9. The dilution device of claim 1, wherein the outlet portion comprises a plurality of outlet portion segments radially distributed around the surface of the first component.

10. The dilution device of claim 9, wherein the plurality of outlet portion segments are evenly spaced with respect to each other.

* * * * *